US012564522B2

(12) United States Patent
Surushe et al.

(10) Patent No.: US 12,564,522 B2
(45) Date of Patent: Mar. 3, 2026

(54) PANT-TYPE ABSORBENT ARTICLE WITH WAIST GUARD

(71) Applicant: The Procter & Gamble Company, Cincinnati, OH (US)

(72) Inventors: Abhishek Prakash Surushe, Kelkheim (DE); Lan Luan, Frankfurt am Main (DE); Qiuxia Yang, Schwalbach am Taunus (DE); Ekaterina Ponomarenko, Mechernich (DE); Wolfgang Edgar Huhn, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 632 days.

(21) Appl. No.: 17/724,529

(22) Filed: Apr. 20, 2022

(65) Prior Publication Data

US 2022/0339044 A1     Oct. 27, 2022

Related U.S. Application Data

(60) Provisional application No. 63/177,405, filed on Apr. 21, 2021.

(51) Int. Cl.
*A61F 13/494* (2006.01)
*A61F 13/49* (2006.01)
*A61F 13/496* (2006.01)

(52) U.S. Cl.
CPC .. *A61F 13/49466* (2013.01); *A61F 13/49011* (2013.01); *A61F 13/4942* (2013.01); *A61F 13/496* (2013.01); *A61F 2013/49092* (2013.01)

(58) Field of Classification Search
CPC .......... A61F 13/49466; A61F 13/49011; A61F 13/4942; A61F 13/496; A61F 2013/49092
See application file for complete search history.

(56) References Cited

U.S. PATENT DOCUMENTS

| | | | |
|---|---|---|---|
| 4,938,755 | A | 7/1990 | Foreman |
| 5,030,303 | A | 7/1991 | Cucuzza |
| 5,569,227 | A | 10/1996 | Vandemoortele et al. |
| 5,904,675 | A | 5/1999 | Laux |
| 8,518,010 | B2 | 8/2013 | Kuwano et al. |
| 8,939,956 | B2 | 1/2015 | Mukai |
| 9,023,006 | B2 | 5/2015 | Takino et al. |

(Continued)

FOREIGN PATENT DOCUMENTS

| | | |
|---|---|---|
| CN | 1282234 A | 1/2001 |
| CN | 1784192 A | 6/2006 |

(Continued)

OTHER PUBLICATIONS

PCT Search Report and Written Opinion for PCT/US2022/071808 dated Jul. 18, 2022, 17 pages.

(Continued)

*Primary Examiner* — Rebecca E Eisenberg
*Assistant Examiner* — Rachel O'Connell
(74) *Attorney, Agent, or Firm* — Charles R. Matson

(57) ABSTRACT

Disclosed is a pant type absorbent article having a waist guard on the back elastic belt, wherein the waist guard comprises a waist guard elastic portion. The absorbent article has a Blowout Percent Leakage of less than 1% when subjected to the Blowout Method herein.

16 Claims, 7 Drawing Sheets

(56) References Cited

U.S. PATENT DOCUMENTS

| | | | |
|---|---|---|---|
| 9,107,778 | B2 | 8/2015 | Sasayama et al. |
| 10,406,040 | B2 | 9/2019 | Chatterjee |
| 11,607,350 | B2 | 3/2023 | Morimoto et al. |
| 2002/0045876 | A1 | 4/2002 | Suzuki |
| 2002/0058922 | A1 | 5/2002 | Skog |
| 2002/0120248 | A1 | 8/2002 | Onishi et al. |
| 2002/0183706 | A1 | 12/2002 | Valentin |
| 2003/0114819 | A1 | 6/2003 | Sayama et al. |
| 2003/0230378 | A1 | 12/2003 | Olsson et al. |
| 2007/0123834 | A1 | 5/2007 | Mcdowall et al. |
| 2010/0318054 | A1 | 12/2010 | Langdon et al. |
| 2012/0311770 | A1 | 12/2012 | Nakajima |
| 2013/0310797 | A1 | 11/2013 | Zink |
| 2014/0031782 | A1 | 1/2014 | Ichikawa et al. |
| 2015/0173973 | A1 | 6/2015 | Lavon et al. |
| 2015/0182388 | A1 | 7/2015 | Katsuragawa et al. |
| 2015/0320612 | A1 | 11/2015 | Seitz |
| 2016/0270975 | A1 | 9/2016 | Surushe et al. |
| 2016/0270977 | A1 | 9/2016 | Surushe et al. |
| 2016/0270979 | A1 | 9/2016 | Raycheck et al. |
| 2016/0287449 | A1* | 10/2016 | Surushe ............ A61F 13/49413 |
| 2017/0000658 | A1* | 1/2017 | Chatterjee ......... A61F 13/49011 |
| 2017/0143560 | A1 | 5/2017 | Morimoto et al. |
| 2017/0246055 | A1 | 8/2017 | Barnes |
| 2018/0071155 | A1 | 3/2018 | Bishop |
| 2018/0104116 | A1 | 4/2018 | Bishop et al. |
| 2018/0221219 | A1* | 8/2018 | Morimoto ............ A61F 13/496 |
| 2018/0289562 | A1 | 10/2018 | Inoue |
| 2019/0350771 | A1 | 11/2019 | Chatterjee |
| 2020/0197560 | A1* | 6/2020 | Buchalter ......... A61F 13/15252 |
| 2021/0093193 | A1 | 4/2021 | Birkner |
| 2021/0100695 | A1 | 4/2021 | Ishibashi et al. |
| 2021/0113388 | A1 | 4/2021 | Matsui |
| 2021/0267815 | A1* | 9/2021 | Gao ................. A61F 13/49014 |
| 2022/0362068 | A1 | 11/2022 | Luan et al. |
| 2022/0362069 | A1 | 11/2022 | Gao et al. |
| 2022/0362070 | A1 | 11/2022 | Gao et al. |
| 2024/0082073 | A1* | 3/2024 | Mun ..................... A61F 13/496 |

FOREIGN PATENT DOCUMENTS

| | | | |
|---|---|---|---|
| CN | 1903152 | A | 1/2007 |
| CN | 101785729 | A | 7/2010 |
| CN | 103282000 | A | 9/2013 |
| CN | 104349756 | A | 2/2015 |
| CN | 205054607 | U | 3/2016 |
| CN | 107405232 | A | 11/2017 |
| CN | 107427395 | A | 12/2017 |
| CN | 107427403 | A | 12/2017 |
| CN | 107820419 | A | 3/2018 |
| CN | 107920934 | A | 4/2018 |
| CN | 108093621 | A | 5/2018 |
| CN | 108601690 | A | 9/2018 |
| CN | 109758299 | A | 5/2019 |
| CN | 109982669 | A | 7/2019 |
| CN | 110290772 | A | 9/2019 |
| EP | 2529717 | A1 | 12/2012 |
| EP | 3162337 | A1 * | 5/2017 ........... A61F 13/495 |
| EP | 3287108 | A1 | 2/2018 |
| EP | 3351227 | A1 | 7/2018 |
| JP | 07184955 | A | 7/1995 |
| JP | H08154971 | A | 6/1996 |
| JP | 2001212176 | A | 8/2001 |
| JP | 2001252303 | A | 9/2001 |
| JP | 2006263306 | A | 10/2006 |
| JP | 2008237391 | A | 10/2008 |
| JP | 2009207778 | A | 9/2009 |
| JP | 2009219627 | A | 10/2009 |
| JP | 2011156110 | A | 8/2011 |
| JP | 2016112208 | A | 6/2016 |
| JP | 3211442 | U | 6/2017 |
| JP | 2018061839 | A | 4/2018 |
| JP | 2018082865 | A | 5/2018 |
| JP | 2018104116 | A | 7/2018 |
| JP | 2018108337 | A | 7/2018 |
| JP | 2018118093 | A | 8/2018 |
| JP | 2019115461 | A | 7/2019 |
| JP | 2020135072 | A | 8/2020 |
| WO | 0072791 | A1 | 12/2000 |
| WO | 2006017718 | A1 | 2/2006 |
| WO | 2009084643 | A1 | 7/2009 |
| WO | 2011087503 | A1 | 7/2011 |
| WO | 2012105212 | A1 | 8/2012 |
| WO | 2016029655 | A1 | 3/2016 |
| WO | 2016159983 | A1 | 10/2016 |
| WO | 2016170909 | A1 | 10/2016 |
| WO | 2017003423 | A1 | 1/2017 |
| WO | 2018123154 | A1 | 7/2018 |
| WO | 2018152834 | A1 | 8/2018 |
| WO | 2019038956 | A1 | 2/2019 |
| WO | 2019073684 | A1 | 4/2019 |
| WO | 2021168782 | A1 | 9/2021 |
| WO | 2021170026 | A1 | 9/2021 |

OTHER PUBLICATIONS

All Office Actions, U.S. Appl. No. 17/180,978.
All Office Actions; U.S. Appl. No. 19/205,029, filed May 12, 2025.
Unpublished U.S. Appl. No. 19/205,029, filed May 12, 2025, to Xu Gao et al.

* cited by examiner

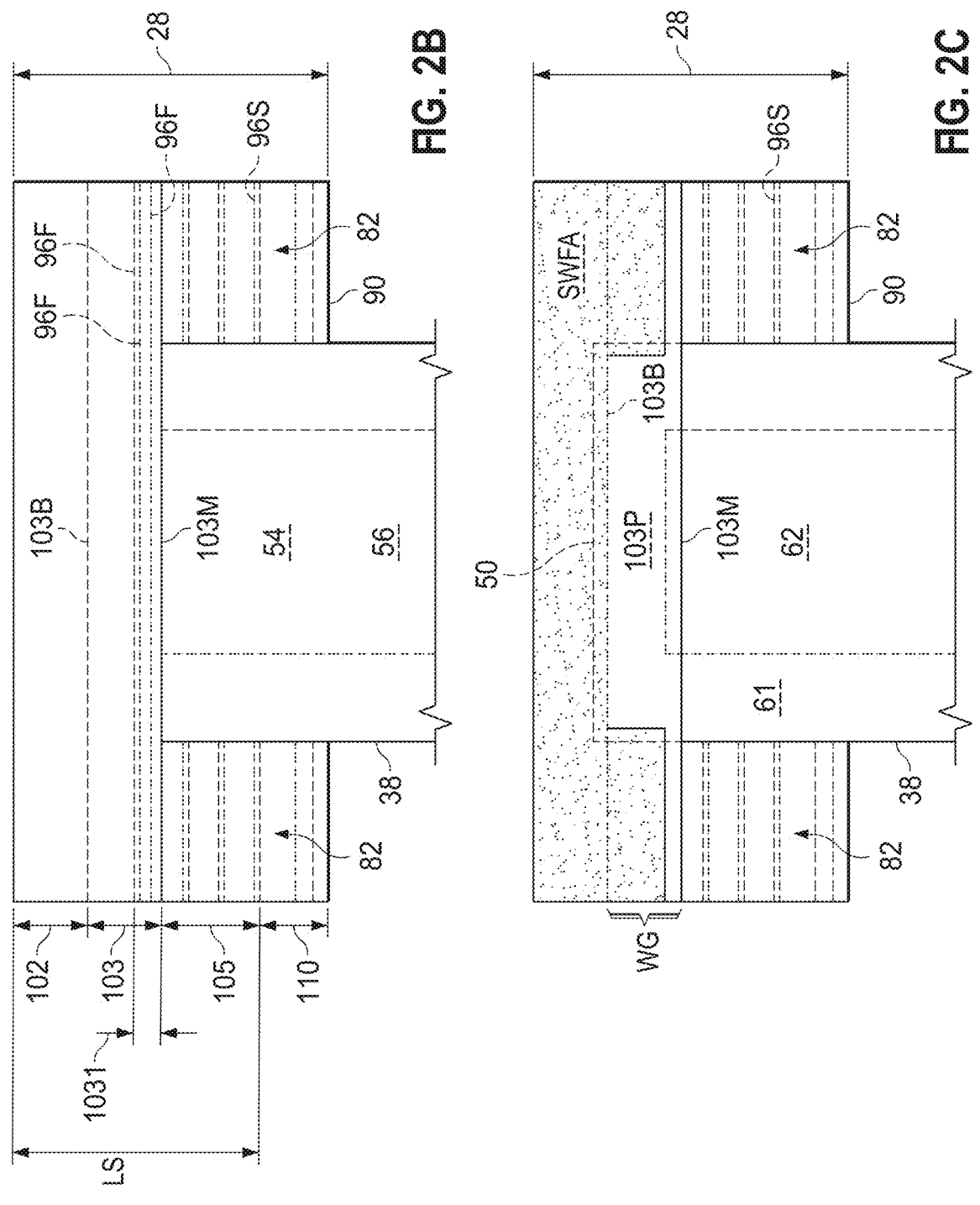

PANT-TYPE ABSORBENT ARTICLE WITH WAIST GUARD

CROSS-REFERENCE TO RELATED APPLICATIONS

This application claims the benefit, under 35 USC 119(e), of U.S. Provisional Patent Application No. 63/177,405, filed on Apr. 21, 2021, which is herein incorporated by reference in its entirety.

FIELD OF THE INVENTION

The present invention relates to pant-type absorbent articles having a waist guard for preventing leakage of low viscosity bodily exudates, while also maintaining other functions as a pant-type wearable article.

BACKGROUND OF THE INVENTION

Infants and other individuals wear absorbent articles such as diapers to receive and contain urine and other body exudates. Pull-on absorbent articles, or pant-type absorbent articles, such as described in PCT Publication WO 2006/17718A, are those which are donned by inserting the wearer's legs into the leg openings and sliding the article up into position about the lower torso. Pant-type absorbent articles have become popular also for younger babies requiring a soft fit around the waist opening and leg openings. Moreover, pant-type absorbent articles have become popular for females having heavy flow or overnight usage during menstruation periods. One function desired for a pant-type article is a protective measure for preventing leakage of low viscosity bodily exudates through the waist opening. Those pant-type articles having less material around the waist opening for breathability purpose or otherwise, may have risk of leakage from the waist opening, particularly when the wearer is lying on his/her back or belly.

Pant-type articles may take various structures wherein the circumference of the waist opening and vicinity thereof is made elastic enough to facilitate the wearer or the caregiver to expand the article and insert the wearer's legs into the leg openings for wearing the article. Accordingly, pant-type articles provide only a very small range of size adjustment or body configuration adjustment based on the structural limitations of the article. As such, pant-type articles are typically so configured to accommodate size and configuration ranges by providing the elastic belt region very stretchable and comfortable to wear, yet with reliable fit such that sufficient protection against sagging and leakage may be provided. It is desired that such basic functions of the elastic belt region may be maintained even with introduction of the aforementioned protective measure.

Based on the foregoing, there is a need for an absorbent article provided with a protective measure for efficiently preventing leakage of low viscosity bodily exudates from the waist opening. There is also a need for providing such an absorbent article which can be economically made.

SUMMARY OF THE INVENTION

The present invention is directed to an absorbent article having a longitudinal direction and a transverse direction comprising a front elastic belt, a back elastic belt, a crotch region, a waist opening, and a pair of leg openings; the crotch region extending longitudinally between the front elastic belt and the back elastic belt.

The absorbent article comprises an absorbent main body extending the entire longitudinal dimension of the crotch region and further extending partly into each of the front elastic belt and the back elastic belt. The absorbent main body comprises a liquid pervious topsheet, a liquid impervious backsheet, and an absorbent material region sandwiched therebetween.

The entirety of the length of the transverse edges of the front elastic belt is seamed with a certain length of the transverse edges of the back elastic belt to define a pair of side seams having a seam length LS. The side seams may have a seam length LS of at least 90 mm, or at least 100 mm, or at least 110 mm, or at least 115 mm. The seam length LS may not be more than 180 mm, or may not be more than 170 mm.

The back elastic belt is divided into multiple zones spanning in the transverse direction and defined by its location from the distal edge (i.e. the edge which forms a portion of the waist opening) to the proximal edge (i.e. the edge which forms is more proximate to the crotch region than the distal edge) relative to the percentage of the seam length LS wherein the distal edge is considered 0% and the proximal edge is considered 100%.

A waist guard is disposed such that the waist guard extends towards the crotch region from a closed base line towards an open edge, wherein the waist guard is partially bonded to the back elastic belt to define a pocket, wherein the complete pocket is provided within a location of from about 5% to about 60% of LS and the area of the pocket superposes the backsheet.

The front elastic belt may be rectangular. The back elastic belt may also be rectangular. The front and back elastic belt may be seamed along the pair of side seams such that their distal edges together form a continuous waist opening and the proximal edge of the back elastic belt is closer to the transverse axis of the article than the proximal edge of the front elastic belt.

The waist guard comprises a waist guard elastic portion (WGEP). The waist guard elastic portion may be provided in the area defining the pocket. The area of the back elastic belt which superposes the waist guard elastic portion is defined as a correlated portion. The tensile stress of the waist guard elastic portion is different than that of the correlated portion. The waist guard elastic portion (WGEP) may have a longitudinal dimension of no greater than about 60 mm, or may have a longitudinal dimension of no greater than 40 mm. The longitudinal dimension of the WGEP may be at least 20 mm, or at least 22 mm. The longitudinal dimension of the WGEP may be not more than 35 mm, or not more than 30 mm. If the longitudinal dimension of the WGEP is too small, the waist guard may not provide sufficient void volume to capture low viscosity bodily extrudes. In the present invention, the void volume of the absorbent article in the back belt is defined in terms of the Blowout Percent Leakage of the absorbent article. The absorbent article has a Blowout Percent Leakage of less than 4.0%, or less than 3.0%, or less than 2.0%, or less than 1.0%, or less than 0.8% when subjected to the Blowout Test Method set out herein.

It has been found that in order to effectively capture low viscosity bodily extrudes, waist guard of the absorbent article should be configured such that the absorbent article has a Blowout Percent Leakage of less than 4%. For the test, a representative amount of artificial low viscosity bodily extrudes have been provided in the absorbent article and a test protocol has been set up which reflects in-use conditions when the article is applied on a wearer and the bodily extrudes are trapped between the skin of the wearer and the absorbent article. The extrudes are squeezed towards the back waist edge. By providing a properly configured waist guard, most or all of the low viscosity bodily extrudes are captured within the waist guard, thus preventing the extrudes from leaking out of the absorbent article along the back waist edge. If the pocket formed within the waist guard is positioned too low (i.e. too much proximate towards the crotch region), the bodily extrudes cannot be captured properly: A part or most of the bodily extrudes may end up between the skin and the pocket, as they cannot enter the pocket because the open edge of the pocket is too low. Also, if the pocket is too small, it provides too little void volume to work effectively.

The absorbent article may have an Efficiency Factor of less than 15% when subjected to the Blowout Method herein. The Efficiency Factor takes the dry weight of the absorbent article into consideration. The dry weight of the absorbent article may be less than 50 g. The dry weight means the weight of the absorbent article prior to use or any testing and is determined after the absorbent article has been conditioned at 23° C.±3° C. and 50%±2% relative humidity at least two hours.

The absorbent article may also comprise barrier leg cuffs, which can also contribute to capturing and "trap" bodily extrudes.

While it has hitherto been believe that the tensile stress of the waist guard elastic portion (as determined by the Belt Zone Tensile Stress Measurement set out herein) should be relatively high and higher than the tensile stress of the correlated portion to enable proper opening of the pocket during use, it has now been surprisingly found that the pocket also works very well (as reflected by the very low Blowout Percent Leakage) also when the tensile stress of the waist guard elastic portion is indeed lower than the tensile stress of the correlated portion. Having a pocket with a tensile stress lower than that of the correlated portion provides a more comfortable absorbent article, as the forces applied on the wearer's skin in the area of the waist guard elastic portion can be reduced. Even the correlated portion, which may have a higher tensile stress than the waist guard elastic portion, applies higher force on the skin vs. the forces applied by the waist guard elastic portion, those forces are "cushioned" by the waist guard elastic portion between the correlated portion and the skin of the wearer when the article is in use.

The waist guard elastic portion may have a tensile stress of 20-70 N/m, preferably from 20 N/m to 60 N/m, or from 20 N/m to 50 N/m, as measured in accordance with the Belt Zone Tensile Stress Measurement set out herein To ensure overall good fit of the absorbent article, the absorbent article of the present invention has a Waist Circumference Force of more than 5.6 N, or more than 5.7 N, as measured in accordance with the Waist Circumference Force test methods set out herein. The absorbent article may have a Waist Circumference Force of less than 20 N, as measured in accordance with the Waist Circumference Force test methods set out herein.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

FIGS. 2B-2C are schematic plan views of one belt embodiment of the present invention with the seams unjoined and in a flat uncontracted condition showing the body facing surface.

DEFINITIONS

Figure 1:
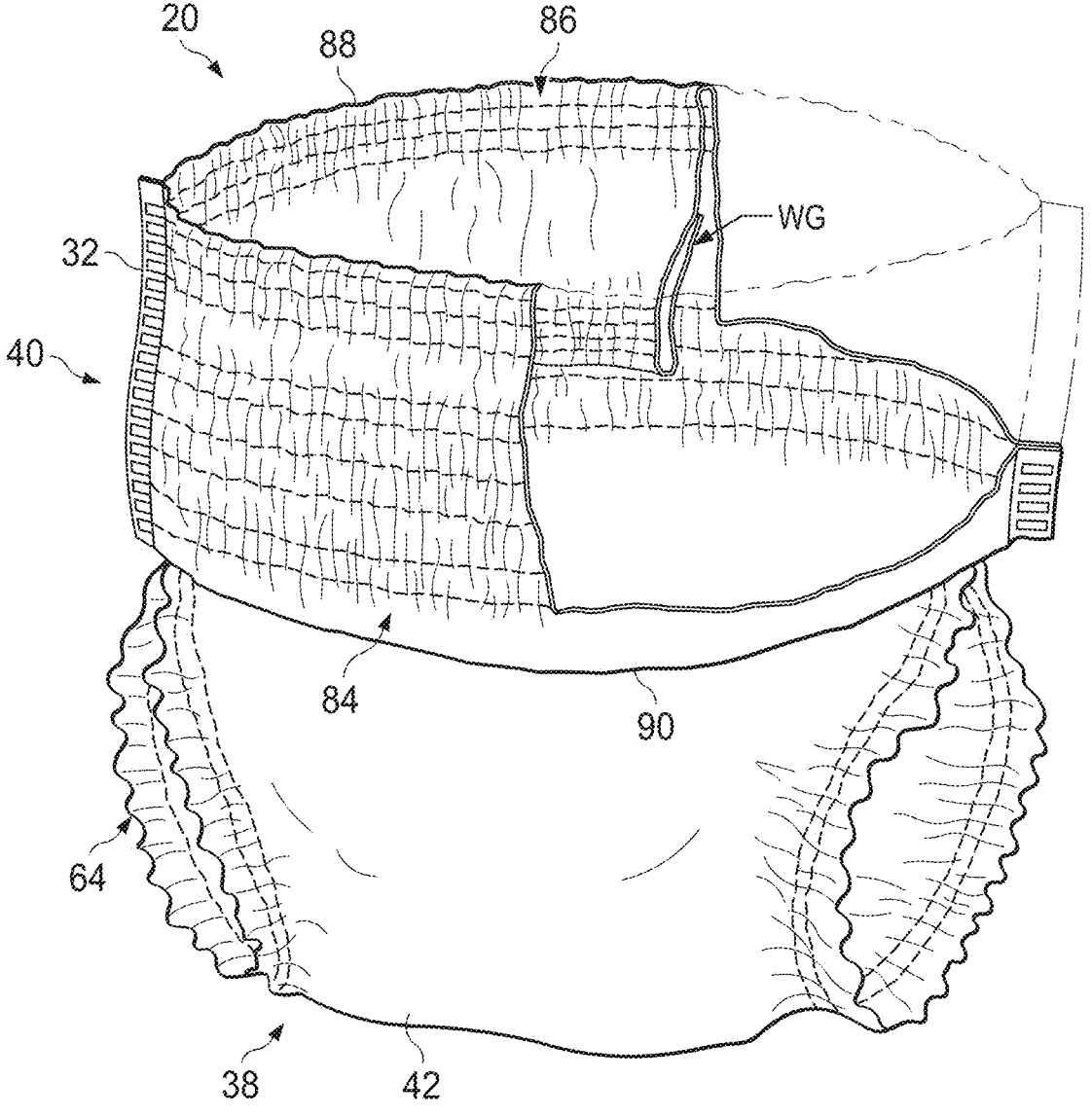
FIG. 1 is a perspective view of one embodiment of an absorbent article of the present invention.

As used herein, the following terms shall have the meaning specified thereafter: "Absorbent article" refers to articles of wear which may be in the form of pants, taped diapers, incontinent briefs, feminine hygiene garments, and the like, so configured to also absorb and contain various exudates such as urine, feces, and menses discharged from the body. The "absorbent article" may serve as an outer cover adaptable to be joined with a separable disposable absorbent insert for providing absorbent and containment function, such as those disclosed in PCT publication WO 2011/087503A.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Dimension", "Length", "Width", "Pitch", "Diameter", "Aspect Ratio", "Angle", and "Area" of the article are all measured in a state wherein the article is extended to the Full Stretch Circumference W1 according to the "Whole Article Force Measurement" herein, and utilizing a ruler or a loupe, unless specified otherwise.

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having a L* value of at least 94, an a* value equal to 0±2, and a b* value equal to 0±2 according to the CIE L* a* b* color system.

DETAILED DESCRIPTION OF THE INVENTION

Figure 2A:
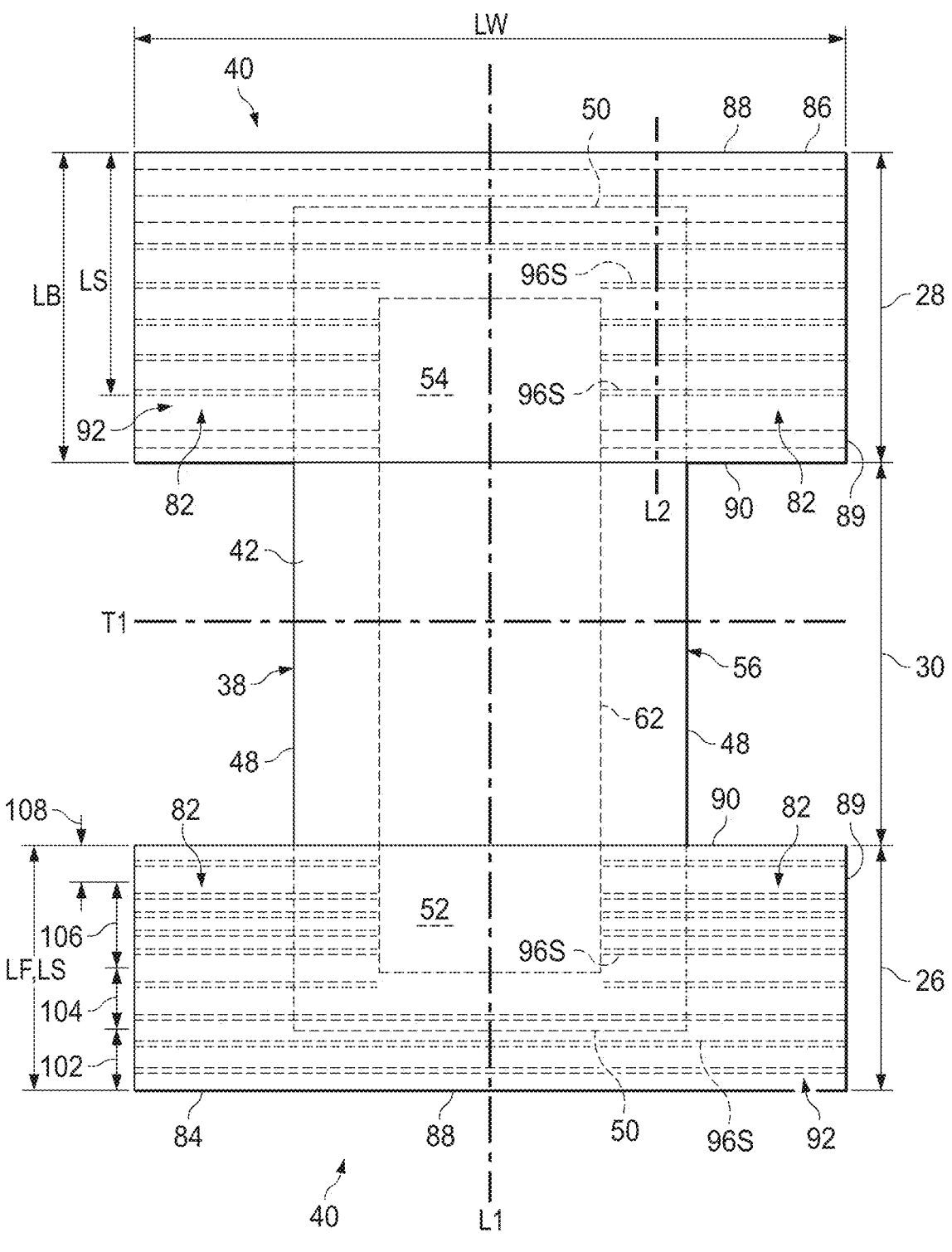
FIG. 2A is a schematic plan view of one embodiment of an absorbent article of the present invention with the seams unjoined and in a flat uncontracted condition showing the garment facing surface.

FIG. 1 is a perspective view of an absorbent article (20) of the present invention, and FIG. 2A is a schematic plan view of an absorbent article with the seams unjoined and in its flat uncontracted condition showing the garment-facing surface. The absorbent article (20) has a longitudinal centerline L1 which also serves as the longitudinal axis, and a transverse centerline T1 which also serves as the transverse axis. The absorbent article (20) has a body facing surface, a garment facing surface, a front elastic belt (84), a back elastic belt (86), a crotch region (30), and side seams (32) which join the front elastic belt (84) and the back elastic belt (86), to form two leg openings and a waist opening.

The absorbent article (20) may be a belt-type pant as in FIGS. 1 and 2A-2C comprising an absorbent main body (38) to cover the crotch region (30) of the wearer, a front elastic belt (84) and a back elastic belt (86) (hereinafter may be referred to as "front and back elastic belts"), the front and back elastic belts (84, 86) forming a discrete ring-like elastic belt (40) extending transversely defining the waist opening and being discontinuous in the longitudinal direction. For the belt-type pant, the discrete ring-like elastic belt (40) may also be referred to as the elastic belt (40). For the belt-type pant as in FIGS. 1 and 2A-2C, the front and back elastic belts (84, 86) and the absorbent main body (38) jointly define the leg openings. For the belt-type pant, the front elastic belt (84) is the front region (26), and the back elastic belt (86) is the back region (28), and the remainder is the crotch region (30).

While not shown, the absorbent article (20) may be a uni-body type pant configured such that the outer cover layer of the absorbent main body (38) and the garment facing layer of the elastic belt (40) are common. For the uni-body type pant, the portion extending in the transverse direction between the side seams (32), respectively, are considered the front region (26) and the back region (28), and the remainder is the crotch region (30). For the uni-body type pant, the front region (26) is considered the front elastic belt (84), and the back region (28) is considered the back elastic belt (86).

The absorbent main body (38) comprises a topsheet, a backsheet and an absorbent material region (62) disposed between the topsheet and the backsheet. The absorbent main body (38) may further comprise an outer cover layer (42) for covering the garment-facing side of the backsheet. The topsheet may be a water permeable substrate. The backsheet may be a water impermeable film. The outer cover layer (42) may be a nonwoven sheet. The absorbent main body (38) comprises an absorbent material region (62) for absorbing and containing body exudates disposed on the absorbent main body (38), and an absorbent material non-existing region (61) surrounding the periphery of the absorbent material region (62). The area adjacent the front and back longitudinal end edges of the absorbent main body (38) comprise the backsheet. The absorbent material non-existing region (61) may be made of the topsheet and/or the backsheet and/or the outer cover layer (42) and/or other parts configuring the absorbent main body (38). In the embodiment shown in FIGS. 2A-2C, the absorbent main body (38) has a generally rectangular shape, left and right longitudinally extending side edges (48) and front and back transversely extending end edges (50). The absorbent material region (62) may exist through the entire longitudinal dimension of the crotch region and extending at least partly in the front and back regions (26, 28). The absorbent main body (38) may have a front waist panel (52) positioned in the front region (26) of the absorbent article (20), a back waist panel (54) positioned in the back region (28), and a crotch panel (56) between the front and back waist panels (52, 54) in the crotch region (30). The center of the front elastic belt (84) is joined to a front waist panel (52) of the absorbent main body (38), the center of the back elastic belt (86) is joined to a back waist panel (54) of the absorbent main body (38), the front and back elastic belts (84, 86) each having a left side panel and a right side panel (82) where the absorbent main body (38) does not overlap. The absorbent main body (38) has a crotch panel (56) positioned between the front waist panel (52) and the back waist panel (54). In a belt-type pant, the front elastic belt is indirectly joined to the back elastic belt along the longitudinal dimension by the absorbent main body.

The absorbent material region (62) may comprise an absorbent layer and an acquisition layer. The absorbent layer is the region wherein absorbent materials having a high retention capacity, such as superabsorbent polymers, are present. The absorbent layer may be substantially cellulose free. Superabsorbent polymers of the absorbent layer may be disposed between first and second layers of material immobilized by a fibrous layer of thermoplastic adhesive material. The first and second layers of materials may be nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process. The acquisition layer facilitates the acquisition and the distribution of body exudates and may be placed between the topsheet and the absorbent layer. The acquisition layer may include cellulosic fibers.

The absorbent layers may be disposed in plurality in the absorbent material region (62). Some portions of the absorbent layers may be configured to have substantially no absorbent material to form a channel or a plurality of channels. Channels may be useful for allowing the absorbent material region (62) to bend upon swelling with fluids, such that the absorbent article conforms to the wearer's body after swelling and prevent sagging of the article. The channels may also be formed in the acquisition layer, and may be configured to at least partly match the channels of the absorbent layer in the thickness direction.

Referring to FIG. 1, the absorbent main body (38) may comprise leg cuffs (64) made of material having high fluid impermeability, and elasticized to provide a barrier along both transverse edges of the absorbent main body (38). Such leg cuffs (64) may be attached to the remainder of the absorbent main body by bonding them to the topsheet at both longitudinal edges of the absorbent main body (38), such that at least in the crotch region (30), the leg cuffs are in active elasticity to provide gasketing around the leg openings.

The elastic belt (40) of the article of the present invention acts to dynamically create fitment forces and to distribute the forces dynamically generated during wear. The front and back elastic belts (84, 86) may be joined with each other only at the side edges (89) to form side seams (32), a waist opening and two leg openings. Each leg opening may be provided with elasticity around the perimeter of the leg opening. The elasticity around the leg opening may be provided by the combination of elasticity from the front elastic belt (84), the back elastic belt (86), and the leg cuffs (64).

The longitudinal length of the backsheet and the outer cover layer (42) may be the same, or may be varied. For example, the outer cover layer (42) may have a shorter length compared to that of the backsheet, such that the outer cover layer (42) is devoid where the absorbent main body (38) overlaps the elastic belt (40). By such configuration, the elastic belt may have better breathability. Further, such configuration may provide cost saving. The transverse width of the backsheet and the outer cover layer (42) may be the same, or may be varied. For example, the backsheet may have a shorter transverse width compared to that of the outer cover layer (42). By such configuration, the longitudinal side edges (48) of the crotch panel (56), which make part of the leg openings, may have better breathability. Further, such configuration may provide cost saving.

For the belt-type pant, the longitudinal length LB of the back elastic belt (86) and the longitudinal length LF of the front elastic belt (84) may be provided the same, or the back elastic belt (86) may have a greater longitudinal length LB as in FIG. 2A. Referring to FIG. 2A, when the wearable article is assembled to form the waist opening and the leg openings, the wearable article (20) is folded along the transverse centerline T1 such that the front distal edge (88) is aligned with the back distal edge (88). The front side edge (89) is also aligned with a portion of the back side edge (89). Then the front elastic belt (84) and the back elastic belt (86) are joined at the front and back side edges (89) at the seams (32). The front and back proximal edges (90), however, may not be aligned to one another. The back proximal edge (90) may be disposed longitudinally closer than the front proximal edge (90) relative to the transverse center line T1 such that the proximal portion of the back side panel (82) extends toward the crotch panel (56) of the main body (38) beyond the front proximal edge (90). The side edge of the proximal portion of the back side panel (82) may not be joined to anywhere and free from attachment. Thus, the proximal portion of the back side panel (82) provides a buttock cover (95) (not shown).

Figures 3A, 3B, 3C, 3D:
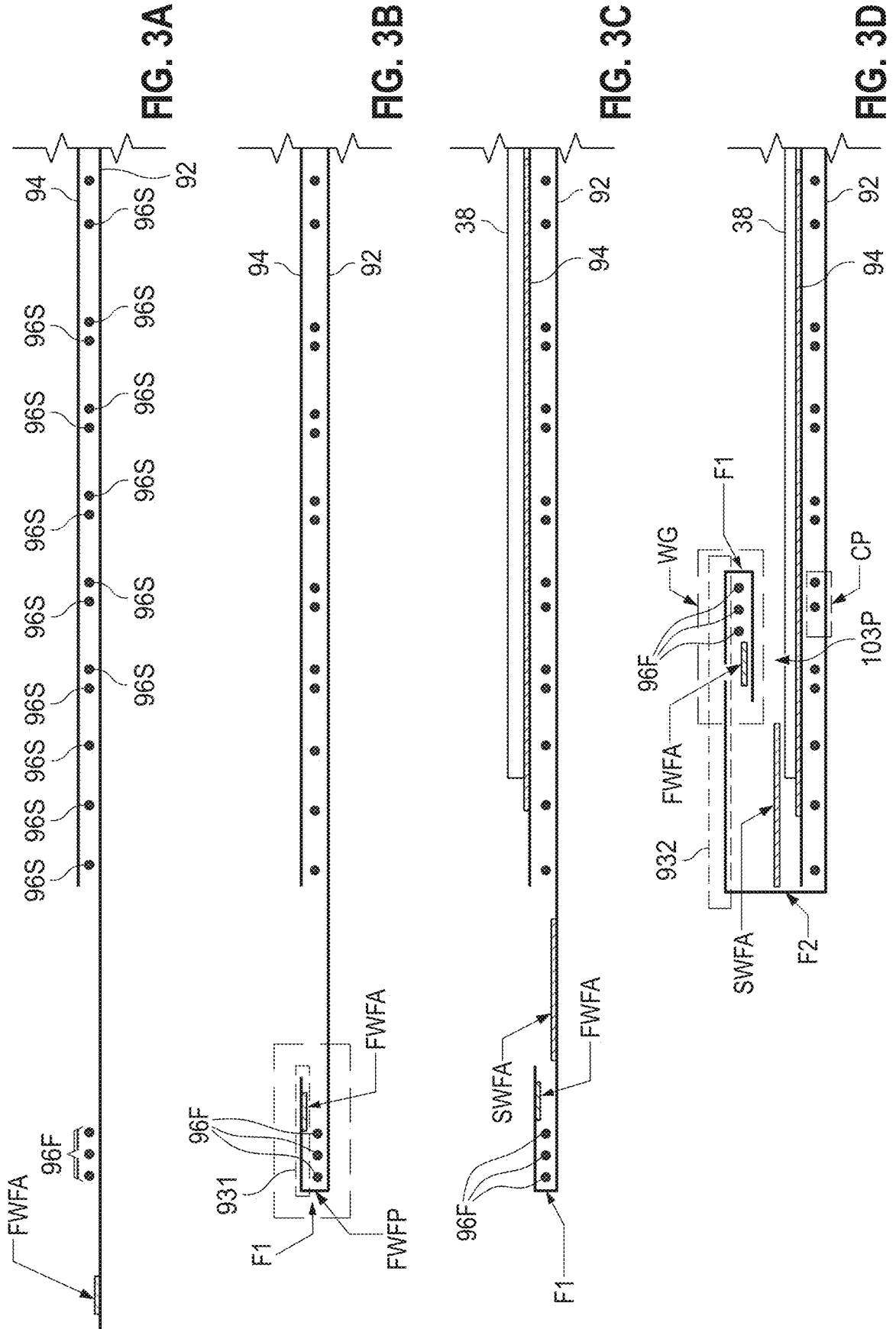
FIGS. 3A-3C are schematic cross section views of precursors for making the embodiment of FIGS. 2A-2C taken along line L2, with the thickness dimension exaggerated.
FIG. 3D is a schematic cross section view of the embodiment of FIGS. 2A-2C, with the thickness dimension exaggerated.

The front elastic belt (84) and back elastic belt (86) are configured to impart elasticity to the belt (40). Referring to FIGS. 1, 2A, and 3D, the front elastic belt (84) and the back elastic belt (86) may each comprise a laminate, the laminate comprising a plurality of elastic members (96F, 96S) running in the transverse direction, an inner sheet (94), an outer sheet (92), and one or a plurality of outer sheet folds (931, 932) wherein the outer sheet fold is an extension of the outer sheet material formed by folding the outer sheet material at the distal edge (88) of the front and back elastic belts or otherwise; wherein the belt elastic members (96F, 96S) are sandwiched between two of these sheets. The front elastic belt (84) and the back elastic belt (86) may each be made only by elastic members (96S), the inner sheet (94), the outer sheet (92), and the outer sheet folds (931, 932). The belt elastic members (96F, 96S) may extend in the transverse direction to provide a ring like elastic belt (40) when the front elastic belt (84) and the back elastic belt (86) are joined. At least some of the elastic members (96F, 96S) extend in the transverse direction substantially parallel to each other. All of the elastic members (96F, 96S) may extend in the transverse direction substantially parallel to each other. Such an article may be economically made. The front and back elastic belt (84, 86) each may have transversely continuous proximal and distal edges, the proximal edge (90) being located closer than the distal edge (88) relative to the longitudinal center of the article. At least 10%, or at least from about 15% to not more than about 70%, of the front and back elastic belts from the waist opening in the longitudinal direction may be a laminate in active elasticity along the entire transverse dimension LW of the front and back elastic belts (84, 86). For each front and back elastic belt (84, 86), the region overlapping the front and/or back waist panel (52, 54) of the absorbent main body (38) may be removed of its elastic activity. Such region removed of elastic activity is referred herein as the "elastic cut window", and the remainder of the intact elastic member capable of imparting elasticity is defined as the "effective length of elasticity of an elastic member".

The tensile stress (N/m) of the entirety of the front and back elastic belts (84, 86), respectively, may be profiled in order to provide the functional benefits of the present invention, such as ease of stretch and application, while also maintaining certain force during wear, to prevent the article from sagging after loading. When the elasticity of the front and back elastic belts (84, 86) are provided by a plurality of elastic members (96F, 96S) running in the transverse direction, the tensile stress may be adjusted by one or more of the following methods; 1) elongation rate of the elastic member (96F, 96S); 2) density (dtex) of the elastic member (96F, 96S); 3) longitudinal pitch of multiple elastic members (96F, 96S); and 4) effective length of elasticity of the elastic member (96F, 96S) in the transverse direction. By elongation, "0% elongation" is meant the original length of the elastic member.

Referring to FIGS. 2A and 2B, the front and back elastic belts (84, 86) may each be divided into multiple zones spanning in the transverse direction and defined by its location from the distal edge (88) to the proximal edge (90) relative to the percentage of the seam length LS wherein the distal edge (88) is considered 0% and the proximal edge (90) is considered 100%. The multiple zones may be configured to provide different tensile stress, or different functions to the front and back elastic belts (84, 86), respectively. In the absorbent article of the present invention, a waist guard WG is disposed. The waist guard WG extends towards the crotch region from a closed base line (103B) toward an open edge (103M). The waist guard WG is partially bonded to the remainder of the back elastic belt (84, 86) to define a pocket (103P). The waist guard WG may be disposed within a location of 25-60% of LS on the back elastic belts (84, 86). FIG. 1 depicts such waist guard WG on the back elastic belt. The waist guard WG may be shorter, such that it spans less than the entire 5-60% of LS. The waist guard WG may be positioned at a dimension of from about 5% to about 55% of LS, or from about 5% to about 50% of LS, or from about 10% to about 55% of LS, or from about 10% to about 50% of LS, i.e. the entire waist guard WG may be provided within these preferred ranges. Without being bound by theory, by providing the waist guard WG in such dimension on the back elastic belt (86), the buttock cleavage of a wearer is effectively covered by the waist guard WG so that low viscosity exudate, such as runny fecal matter or blood, may be effectively drawn into the pocket.

As exemplarily shown in FIGS. 2B, 2C, and 3A-3D (but not limited to embodiments illustrated in these Figures, but applicable to all absorbent articles of the present invention), the waist guard WG may be made by an extension of the outer sheet (92) extending beyond the longitudinal dimension of the inner sheet (94), which extension of the outer sheet (92) is folded inwardly twice in order to encompass at least a first elastic member (96F) and further to provide the waist guard WG in the intended position relative to the side seam length LS. As a result of the two folds (F1 and F2), the at least first elastic member (96F) is sandwiched between the first outer sheet fold (931) and the second outer sheet fold (932), wherein the first outer sheet fold (931) constitutes the garment facing side of the waist guard WG, and the second outer sheet fold (932) constitutes the body facing surface. The second outer sheet fold (932) may be in direct contact with the skin of the wearer when the article is in use. Referring to FIGS. 2C and 3D, a certain longitudinal dimension from the distal edge of the second outer sheet fold (932) may be bonded to the remainder of the belt, such bonding shown as SWFA, however, leaving some longitudinal dimension unbonded. The first outer sheet fold (931) may be bonded to the second outer sheet fold (932), such bonding shown as FWFA. The position provided most distal of the unbonded region is the closed base line (103B), and the common proximal edge of the first outer sheet fold (931) and second outer sheet fold (932) is the open edge (103M). The waist guard WG is defined as having a longitudinal dimension spanning from the closed base line (103B) and the open edge (103M), and having a transverse dimension matching the width of the belt to which it is provided. The left and right transverse edges of the waist guard WG may also be bonded to the remainder of the belt, such bonding shown as SWFA. Preferably the bonding is made by adhesive. The adhesive may be hydropobic, which can help to prevent low viscosity exudate from penetrating out of the pocket nonwoven materials. The adhesive, such as the hydrophobic adhesive, may be a hot melt adhesive. To determine whether a hot melt adhesive is hydrophobic, a portion of the hot melt adhesive is molten and spread on an even, horizontal surface, such as a table, to form a film. Then a drop of water is applied on the fim and the contact angle is determined, as is well known in the art. The adhesive is hydrophobic, if the contact angle of more than 90°. The unbonded region thus provided, and being defined and delimited by the closed base line and the leftand right transverse edges, is the pocket (103P). The bondings provided to define the area of the pocket (103P) are so configured to provide the pocket (103P) substantially superposing the backsheet, preferably completely superposing the backsheet in both in the longitudinal dimension parallel to the longitudinal centerline of the article as well as in the transverse direction parallel to the transverse centerline of the article.

The bonded portion (shown as SWFA) may superpose the backsheet by at least 5 mm, or by at least 10 mm along each of the left and right side edges of the pocket, wherein the respective part of the edge of the bonded portion may delimit and thus define the left and right side edges of the pocket. Moreover, the bonded portion (shown as SWFA) may superpose the backsheet by at least 5 mm, or by at least 10 mm along the closed base line of the pocket, wherein the respective part of the edge of the bonded portion may delimit and thus define the closed base line of the pocket.

Without being bound by theory, by providing the pocket (103P) substantially superposing the backsheet, this prevents low viscosity exudates and/or low surface tension exudates having entered the pocket (103P) from flowing or penetrating out of the pocket (103P) towards the waist opening, or the transverse edges.

Referring to FIG. 2B, the at least first elastic member (96F) provides the waist guard elastic portion WGEP, wherein elasticity may be imparted by one or more elastic strands, elastic ribbons, mechanically activated nonwovens, or otherwise. The waist guard elastic portion WGEP is defined as having a longitudinal dimension (1031) spanning from the open edge (103M) to the distal edge of the at least first elastic member (96F). When the first elastic member (96F) is a plurality of elastic strands, the distal edge of the waist guard elastic portion WGEP is the position of the elastic strand which is positioned most distal (along the longitudinal dimension of the absorbent article) from the open edge of the waist guard. There may be 2-10 elastic strands, or from 2-5 elastic strands, or 2-8 elastic strands, or 3-4 elastic strands, or 3-8 elastic strands, or 4-6 elastic strands disposed on the waist guard elastic portion. The longitudinal dimension of the waist guard elastic portion WGEP may be smaller than that of the waist guard WG such that a pocket (103P) having containment capacity may be provided. The longitudinal dimension of the waist guard elastic portion WGEP may be no greater than about 40 mm, or no greater than about 35 mm, or no greater than about 30 mm, or no greater than about 25 mm, or from 15 mm to about 40 mm, or from about 10 mm to about 35 mm, or from about 10 mm to about 25 mm. The distance between the two elastic strands which are closest to the open edge of the waist guard may be smaller than the distance between any other neighboring elastic strands in the waist guard elastic portion. Alternatively or in addition, the distance between the open edge and the elastic strand closest to the open edge may be the same or smaller than the distance between the two elastic strands which are closest to the open edge of the waist guard. Also alternatively or in addition, the number of elastic strands adjacent the open edge may be higher than the number of elastic strands away from the open edge, wherein "away from the open edge" means the 50% of the pocket which are furthest away from the open edge.

The pocket may have a rectangular shape (as exemplarily shown in FIGS. 2B and 2C), however, the pocket (103P) may take other shapes by changing the bonding area SWFA such that the closed base line (103B), and/or the left and right transverse edges defining the pocket, are shaped. For example, the closed base line (103B) may be concave or convex toward the pocket (103B) to match the wearer's anatomy. The closed base line (103B) of the waist guard may also be straight and parallel to the distal edge of the back elastic belt (86). The left and right transverse edges may be such that the width of the pocket increases or decreases along the longitudinal dimension starting from the closed edge to the open edge of the pocket.

The longitudinal dimension of the pocket (103P) defined as the shortest distance between the closed base line (103B) to the open edge (103M) and extending parallel to the longitudinal centerline of the article may be about 10 mm to about 50 mm, or from about 12 mm to about 40 mm, or from 20 mm to 30 mm. For pockets having a closed base line (103B) which are not straight but, for example, concave or convex, the location on the closed base line (103B) which is closest to the distal edge of the back elastic belt (86) may also be provided within the 55% to 60%, or 5% to 55%, or 5% to 50% or 10% to 50% of LS, as the complete waist guard WG is provided within the 5% to 60% of LS.

The transverse dimension of the pocket (103P) is defined as the longest distance of the pocket extending parallel to the transverse centerline of the article from the left side edge of the pocket to the right side edge of the pocket. The left and right side edges extend between the closed base line and the open edge of the pocket. The transverse dimension of the pocket (=the width of the pocket) may be from 40% to 96%, or from 50% to 95%, or from 60% to 95% of the transverse dimension of the transversely extending edge of the backsheet (=the width of the backsheet), which is provided in the back waist region. The transversely extending edge of the backsheet may extend parallel to the transverse centerline of the absorbent article.

The transverse dimension of the pocket may be from 40 mm to 120 mm, or from 50 mm to 100 m, or from 60 mm to 90 mm. The pocket may have a smallest distance extending parallel to the transverse centerline of the article from the left side edge of the pocket to the right side edge of the pocket, which may be the same as the longest distance of the pocket (such that there is no difference between longest and shortest distance), or the shortest distance of the pocket may be at least 70%, or at least 80%, or at least 90% of the longest distance of the pocket.

By providing the waist guard at a dimension of from about 5% to about 60%, preferably to about 55% and more preferably to about 50% of LS, the waist guard is provided such that the likelihood of the open edge (103M) of the pocket overlaying the gluteal grove of the wearer is reduced. The article of the present invention is (also) suitable for baby/toddler pants which are already more active compared to new born babies. However, increased activity generally leads to a higher likelihood that the article sags, so that the waist edge (=distal edge of the front and back belt) shifts downwardly during use. Thereby, also the waist guard, including its open edge, tends to shift downwardly during use. To address and counterbalance such movement, the open edge may be provided sufficiently high (in the longitudinal dimension, i.e. towards the distal edge of the back belt) to reduce or avoid the risk of overlap of the open edge with the gluteal grove. If the open edge overlaps with the gluteal grove, the pocket may not able be to properly receive fecal material.

As exemplified in FIGS. 2B and 3D (but not limited to embodiments shown in these Figures, but applicable to all absorbent articles of the present invention), the remainder of the belt superposing the waist guard elastic portion WGEP is defined a correlated portion CP. Namely, the correlated portion CP has the same longitudinal dimension (1031) as the waist guard elastic portion WGEP. The correlated portion CP may be elasticized or may not be elasiticized. The tensile stress of the waist guard elastic portion WGEP is different than that of the correlated portion CP. The difference in tensile stress of the waist guard elastic portion WGEP to the correlated portion CP may be at least about 25%, or at least about 50%. Without being bound by theory, such tensile stress difference enables the waist guard elastic portion WGEP to be in close contact with the wearer, while pulling away the open edge (103M) from the correlated portion CP, thus opening the pocket (103P) towards the proximal side. Thus, the pocket (103P) is configured to have good containment capacity. The correlated portion CP may have an elastic cut window such that some portion is elasticized, while the transverse center does not interfere with the opening of the pocket (103P). When the waist guard elastic portion WGEP is elasticized by disposing a plurality of elastic strands (96F), one elastic strand is disposed from no less than 2 mm to 5 mm away from the open edge (103M). Placement of the elastic strand on the very edge of the open edge (103M) may be avoided in order to prevent the waist guard position WG causing irritation to the wearer. The waist guard elastic portion WGEP may be disposed with a plurality of elastic strands (96F) with a relatively small pitch between each other. The elastic strands (96F) of the waist guard elastic portion WGEP may be disposed at a pitch of no more than about 12 mm, or no more than about 10 mm, or no more than about 6 mm, or between about 2 mm to about 8 mm, or between about 3 mm to about 9 mm, or between about 2 mm to about 6 mm The elastic strands (96F) for providing the waist guard elastic portion WGEP may be provided in color such that the existence and function of the waist guard WG is clearly communicated to the wearer or caregiver. At least 2 of the elastic strands for providing the waist guard elastic portion WGEP may have a color which is visible from the body facing side of the article. The color may be selected from green, blue, purple, or a combination thereof, in order to be easily recognized, while not being confused with the color of containment. The same or similar color may be used for other elastic strands (96S) disposed on the belt to provide a coordinated appearance. For example, those elastic strands on the front waist zone (102) or the back waist zone (102) may have the same or similar color.

The waist guard WG may be configured in a certain way relative to the absorbent main body to provide improved function. As mentioned above, the area of the pocket (103P) are so configured to provide the pocket (103P) substantially superposing the backsheet, preferably completely superposing the backsheet. As exemplified in FIGS. 2C and 3D (but not limited to the embodiments shown in these Figures, but applicable to all absorbent articles of the present invention), the longitudinal edges of the absorbent main body (38) may be positioned and bonded between the waist guard WG and the remainder of the belt. This is to avoid having sharp edges of the absorbent main body (38) on the body facing surface, and also to avoid leakage from the edges. The absorbent main body (38) comprises an absorbent material region (62) which may be surrounded by an absorbent material non-existing region (61), wherein the absorbent material region (62) having a greater thickness than that of the absorbent material non-existing region (61). The absorbent material region (62) may partially superpose the area of the pocket (103P) to provide at least some absorbent capacity in this region. At least about 3%, or at least about 10%, or at least 20%, or at least 30%, or at least 40% of the area of the pocket (103P) may superpose the absorbent material region (62) toward the proximal edge. Even so, the combined thickness of the waist guard elastic portion WGEP, the correlated portion CP, and the portion of the absorbent main body (38) sandwiched therebetween may be kept to no more than about 5 mm, preferably no more than about 4 mm. This is so that the thickness of the remainder of the article does not interfere with the opening of the pocket (103P) towards the proximal side due to the elasticity of the waist guard elastic portion WGEP.

The belt on which the waist guard WG is disposed may be divided into 3 zones spanning in the transverse direction and defined by its location from the distal edge (88) to the proximal edge (90) relative to the percentage of the seam length LS wherein; 0% to the distal edge of the waist guard WG is a waist zone (102), and the distal edge to the proximal edge of the waist guard WG is a protective zone (103), and the proximal edge of the waist guard WG to 100% is another zone. When there is an elastic member disposed at the distal edge or the proximal edge of the protective zone (103), such elastic member is considered to be included in the protective zone (103). Elastic members may be disposed on the remainder of the protective zone (103) which superposes the unelasticized area of the waist guard WG.

The waist guard WG may be configured in a certain way relative to a pair of leg cuffs (64) disposed along both transverse edges of the absorbent main body (38), to provide improved function. For the belt comprising the waist guard WG, the leg cuffs (64) may be in active elasticity at the point intersecting the open edge (103M). By providing the leg cuffs in active elasticity in such position, the combined elasticity from the leg cuffs and waist guard elastic portion WGEP may help hold the leg cuffs (64) and waist guard WG in close contact with the wearer, and further provide additional containment capacity for the pocket (103P).

As exemplified in FIGS. 2A and 2B (but not limited to the embodiments shown in these Figures, but applicable to all absorbent articles of the present invention), the back elastic belt (86), where the waist guard WG is disposed, may be divided into three zones spanning in the transverse direction and defined by its location from the distal edge (88) to the proximal edge (90) relative to the percentage of the seam length LS wherein; 0% to the distal edge of the waist guard WG is a back waist zone (102), the distal edge to the proximal edge of the waist guard WG is a protective zone (103), and the proximal edge of the waist guard WG to 100% is a buttock zone (105). The back elastic belt may further have a buttock cover zone (110), wherein the longitudinal dimension of the back elastic belt LB exceeds LS. The front elastic belt may be divided into 4 zones wherein: 0-25% is the waist zone (102), 25-50% is the distal tummy zone (104), 50-85% is the proximal tummy zone (106), and 85-100% is the leg zone (108). When there is an elastic member disposed at 25% from the distal edge (88), such elastic member is considered to be included in the waist zone (102). When there is an elastic member disposed at 50% from the distal edge (88), or 85% from the distal edge (88), such elastic member is considered to be included in the proximal tummy zone (106).

Figure 4:
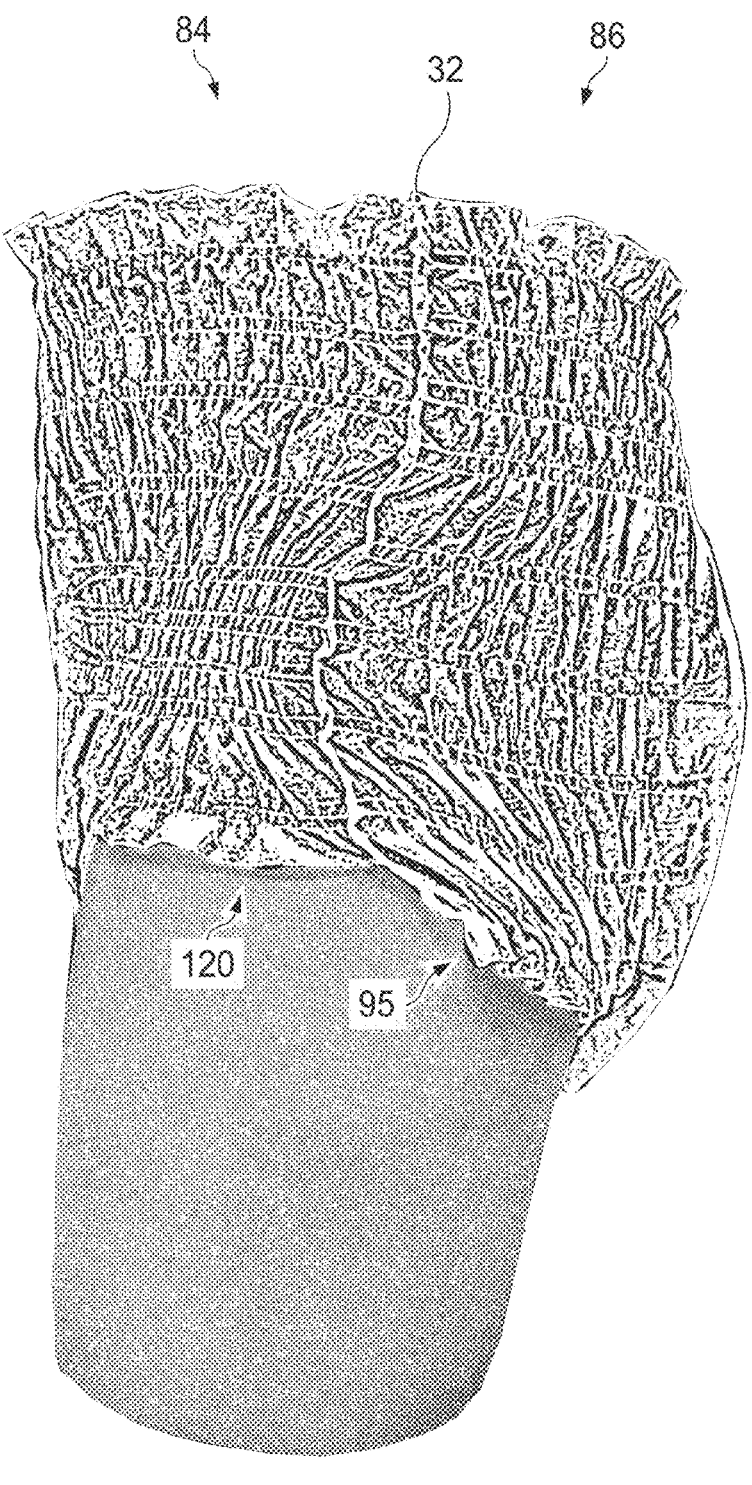
FIG. 4 is a side view of one embodiment of an absorbent article of the present invention worn on a mannequin.

The tensile stress of the protective zone (103) may be provided higher than the tensile stress of either the back waist zone (102), or the buttock zone (105). The tensile stress of the front proximal tummy zone (106) may be provided higher than the tensile stress of any of the front waist zone (102), the front distal tummy zone (104), or the front leg zone (108). The tensile stress of the front proximal tummy zone (106) may be higher than the tensile stress of any other zone, either in the front or the back. When comparing all of the zones of the front elastic belt and the back elastic belt, the tensile stress may be provided greatest in the order of: the front proximal tummy zone (106), followed by the protective zone (103). Without being bound by theory, such profiling of the tensile stress per zone is believed to provide the article of the present invention with a shaped elastic belt (40) that conforms well to a human body, such as in FIG. 4, particularly to a lower torso of a child of less than 36 months of age, and therefore provide good fit and comfort to the wearer, without compromise of sagging prevention or leakage prevention. Namely, the front proximal tummy zone (106) is subject to high tensile stress such that the article may be anchored against the wearer's trochanter, while leaving more area for the buttock zone (105) to accommodate the wearer's buttock.

As exemplified in FIGS. 3A-3D (but not limited to the embodiments shown in these Figures, but applicable to all absorbent articles of the present invention), the elastic belts of the present invention may be made by a relatively simple structure comprising no more than the inner sheet (94), the outer sheet (92), the first outer sheet fold (931), the second outer sheet fold (932), and the first and second elastic members (96F, 96S) encompassed within these layers. The first outer sheet fold (931) may be at least the same length, or may, preferably, be longer than the length of the pocket side edges of the pocket, which is to provide a double layer protection provided by the layers of the outer sheet created by the first and second outer sheet fold. This double layer structure helps to reduce or prevent low viscosity and low surface tension body exudates from penetrating through the pocket from onto the body of the wearer. Any portion of the elastic belt comprising the waist guard WG may be made by less than 6 layers, or made by 3-4 layers, and in a thickness of no more than about 5 mm, or no more than about 4 mm Providing the belt structure simple and relatively thin is advantageous in maintaining breathability and softness of the belt. Further, the elastic belts may be made by elastic strands commonly used in the art having a density of no more than 940 dtex. Certain zones of the belt may be disposed of elastic bodies having a density of no more than about 600 dtex, or not more than 580 dtex, thus providing a soft fit. Elastic bodies having a density of no more than about 500 dtex may be disposed on one or more of the waist zone (102) or the front leg zone (108). Without being bound by theory, it is believed that elastic bodies of relatively low density impart an easy initial stretch experience when stretch opening the article (20), while maintaining a good fit during wear. The article of the present invention may be provided with a protective measure for preventing leakage of low viscosity bodily exudates from the waist opening, while maintaining good stretchability for ease of application, good fit for preventing sagging, good comfort and softness, and good breathability. The present article may have a Waist Circumference Force according to the Whole Article Force Measurement herein of no more than about 9N, or no more than about 8N.

Referring to FIGS. 1, 2A, and 3D, even when the back elastic belt (86) comprises a waist guard WG, the remainder of the back elastic belt (86), and particularly the garment facing surface of the back elastic belt (86), may be maintained in a simple structure. This enables the article to have other functions that are desired of a pant type absorbent article, such as having a disposal tape attached to the garment facing surface of the back elastic belt (86). Accordingly, the absorbent article may be devoid of fastening means.

Barrier Leg Cuffs and Leg Elastics

The absorbent main body of the absorbent article may comprise one or more pairs of barrier leg cuffs 32 (not shown) and one or more pairs of leg elastics (64). The barrier leg cuffs may be positioned laterally inboard of leg elastics (64). Each barrier leg cuff may be formed by a piece of material which is bonded to the absorbent main body so it extends upwards from a wearer-facing surface of the absorbent main body when the absorbent article is worn, and provide improved containment of body exudates approximately at the junction of the torso and legs of the wearer. The barrier leg cuffs are delimited by a proximal edge joined directly or indirectly to the topsheet and/or the backsheet and a free terminal edge, which is intended to contact and form a seal with the wearer's skin. The barrier leg cuffs may extend at least partially between the front and back transversely extending end edges (50) of the absorbent main body along and adjacent to each of the two side edges (48) of the absorbent main body and may be at least present in the crotch region, and may extend into the front and back waist region. The barrier leg cuffs may each comprise one or more elastics (e.g., elastic strands or strips) near or at the free terminal edge. These elastics cause the barrier leg cuffs to help form a seal around the legs and torso of a wearer.

The leg elastics extend at least partially between the two transversely extending end edges (50) of the absorbent main body. The leg elastics essentially cause portions of the absorbent article proximate to the absorbent main body's two (i.e. left and right) side edges (48) to help form a seal around the legs of the wearer. The leg elastics may extend at least within the crotch region 14.

Test Methods

Blowout Test Method

The Blowout is defined as artificial viscous body exudates (called "artificial BM" in this test method) being expelled onto and beyond the waist cuff or waist area of absorbent article. An absorbent article in the pant form (i.e. the type of absorbent articles to which the present invention refers) is cut open along the side seams.

Thereafter, the width of the back elastic belt is measured by applying a weight of 1.000 kg across the side edges formed along the previously cut open side seams of the back elastic belt. One of the side edges of the back elastic belt is clamped centered on the last centimeter of the side edge of the back elastic belt in a flat jaw 5 cm wide fixture with 1 cm clamping depth. It is hung vertically and a 1.000 kg weight is attached to an identical clamp that is provided the same manner and position on the other side edge of the back elastic belt and the weight is slowly released manually. After 30 seconds, the back elastic belt width is measured from clamp to clamp and 2 cm are added to the result. The result is rounded to the next cm.

If the front elastic belt width is significantly different from the width of the back elastic belt (as can easily be assessed by simply stretching out the front and back elastic belt by hand), the width of the front elastic belt is determined in the same manner as the width of the back elastic belt.

The same procedure as described above is used for measuring the length of the absorbent article by applying a weight of 0.300 kg. The absorbent article is clamped across the longitudinal centerline of the absorbent article on the last centimeter of the back waist edge in a flat jaw 15 cm wide fixture (centered on the longitudinal centerline) with 1 cm clamping depth. It is hung vertically and a 0.300 kg weight is attached to an identical clamp that is provided the same manner and position on the front waist edge of the absorbent article and the weight is slowly released manually. The absorbent article length is then measured after 30 second from clamp to clamp and 2 cm are added to the result. The result is rounded to the next cm.

Figure 5:
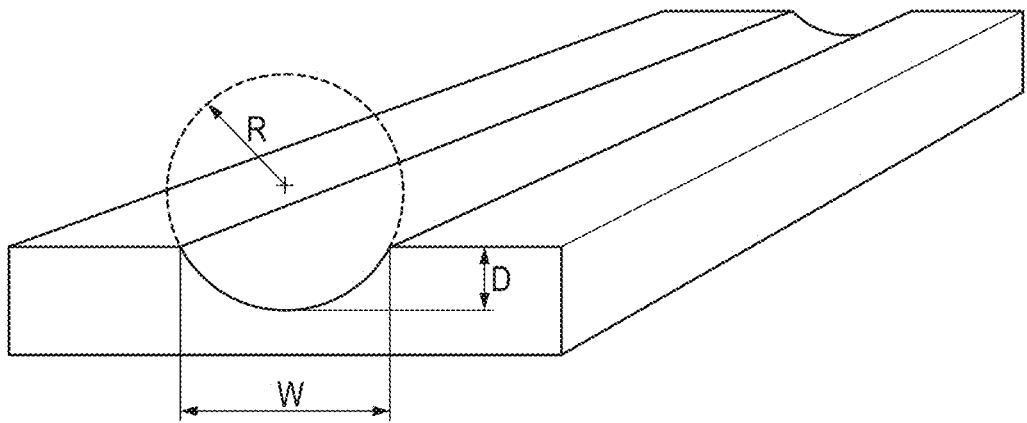
FIG. 5 is a schematic drawing of the measurement trough according to the Blowout Test Method.
Figure 6:
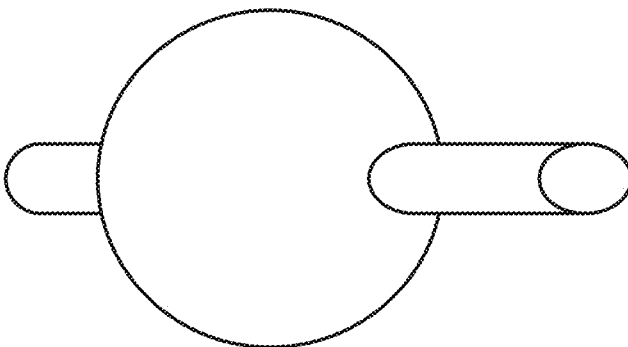
FIG. 6 is a schematic drawing of the testing ball according to the Blowout Test Method

A trough is made from a rectilinear block of rigid material (e.g. nylon) with a flat planar upper surface having a width of at least those of the absorbent article measured above and a length of at least 10 cm more than that of the absorbent article measured above, and at least 5 cm deep. A channel is machined into the block, the channel runs down the middle entire length of the block and is a portion of a circle with a radius R=12.70 cm. The width W of the through is 10.16 cm and the depth D is 2.54 cm (see FIG. 5).

All testing is performed in a room controlled at 23° C.±3° C. and 50%±2% relative humidity. Samples are conditioned at 23° C.±3° C. and 50%±2% relative humidity at least two hours prior to testing.

The absorbent article is laid down in a flat planar configuration, on the upper surface of the block, with the topsheet facing upwards and the back sheet taut, extended to the before measured width and length dimensions and fixed with tape stripes. The longitudinal centerline of the absorbent article is aligned with the center line of the trough. The back waist edge is provided 10 cm inboard from the edge of the through.

Application point for saline and artificial BM is ½ the length of the stretched out absorbent article on the longitudinal centerline. Two paper towels are weighed folded to 15×15 cm and positioned flat at the back waist edge of the absorbent article with 1 cm of the paper towel tucked between the absorbent article and the upper surface of the block at the back waist edge to collect artificial BM.

Saline 9 g of NaCl are dissolved in 1000 ml $H_2$.

Artificial BM is a 0.5% aqueous Solution of Lubrizol 981 (Carbopol)

Preparation of 1000 g

Carbopol (5.0 g+/−0.1 g)

Dist. Water (945.0 g+/−0.1 g) in a 2000 ml beaker

1M NaOH solution (50.0 g+/−0.1 g)

Food colorant, (e.g. available from Kroger® or similar, composition of Kroger® food colorant is water, propylene glycol, yellow 5, red40, blue1 citric acid, sodium benzoate)

Stirring and adding procedure:

Take a 2000 ml beaker with the dist. Water and put a stirrer, (e.g. 3 bladed propeller type with 55 mm diameter) such that the propeller is 2 cm below the water surface.

Start stirring at 1100 rpm

Add the Carbopol uniformly over 10 seconds

Keep stirring at 1100 rpm (for 30 min)

Add the NaOH-solution uniformly over 10 sec.

Add 2 drops of food colorant and keep stirring at 1100 rpm for 30 min.

Quality Check of artificial BM

Equipment:

Brookfield spindle viscometer, or equivalent

Standard 28 mm Brookfield Spindle/22.3° C./RPM 600

Viscosity of the solution has to be between 3300 and 4800 cp for the artificial BM to be used in the Blowout Test.

Procedure

The following amounts of saline and artificial BM are used for absorbent articles of different weight ranges:

For an absorbent article with overall dry weight up to 30.0 g: 2 times 50.0 ml saline and one times 100.0 g artificial BM.

For an absorbent article with overall dry weight equal to or greater than 30.0 g and up to 50.0 g, 2 times 75.0 ml saline and one time 150 g artificial BM.

For an absorbent article with overall dry weight equal to or greater than 50.0 g, 3 times 75.0 ml saline and one time 200 g artificial BM.

The artificial BM is measured by filling a syringe with a 5 mm to 10 mm wide nozzle from a beaker to within +/−0.5 g. Saline is measured volumetrically with a 100 ml syringe. Saline 0.9% is applied with an application rate of 5 ml/sec. Wait time after completed application of 50 ml/75 ml (depending on article dry weight, see above) of saline is 60 sec wait time. Again saline 0.9% (application rate 5 ml/sec) is applied and 60 sec wait time after application is complete.

Then artificial BM is applied with an application rate of 10 ml/sec and given 60 sec wait time after application is complete.

A 10.2 cm diameter ball with a transverse axle (the axle is approximately 26 cm long and has a diameter of 1.5 cm) weighing 580 g total (=ball and axle) is placed on the front waist area 50 mm inboard from the front waist edge of the absorbent article so that the ball is centered in the trough with the axle horizontal and perpendicular to the longitudinal axis of the trough. It is rolled towards the rear manually with 10 cm/s control via stopwatch without applying downward pressure until the axle is 3.00 cm inboard of the back waist edge of the absorbent article. Then the ball is lifted vertically off the absorbent article. The paper towels (with artificial BM that may have been squeezed on the towels) are carefully removed. The same towels are now used to carefully scrape and collect all artificial BM that may be deposited on the upper surface of the absorbent article within the area between the back waist edge and 5 cm in longitudinal direction inboard from the back waist edge (=longitudinal dimension of the area) and as wide as the absorbent main body of the absorbent article (=transverse dimension of the area). Then, the towels are weighed and the Blowout Percentage Leakage is calculated as follows:

Blowout Percent Leakage II % I=((gram leaked artificial BM (collected on the tared paper towel)/ total gram artificial BM applied))*100

3 to 4 replicates on identical absorbent articles are tested. The reported Blowout Percent Leakage [%] is reported as the and report the average of the replicates and is calculated to within +/−0.01%.

Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10 and 90% of capacity of the load cell used. The instrument is calibrated according to the manufacturer's instructions. All testing is performed in a room maintained at 23±2° C. and 50±5% relative humidity.

Figure 7:
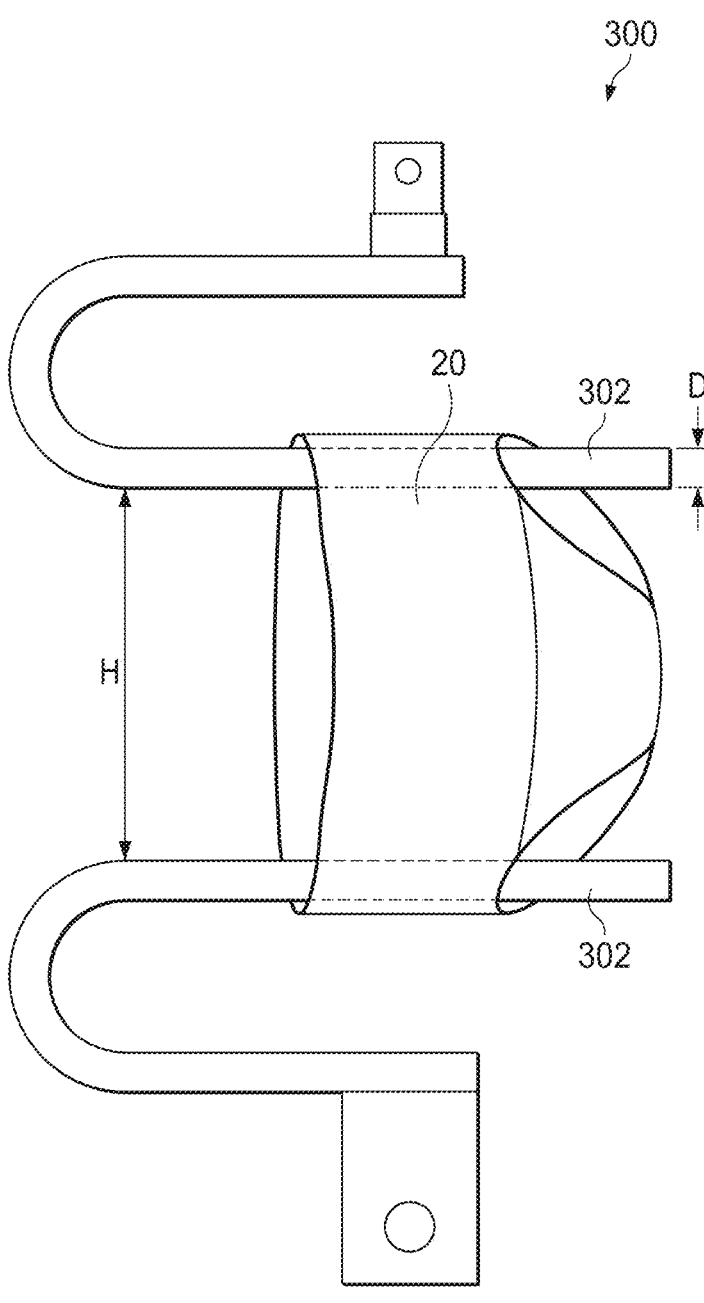
FIG. 7 is a schematic view of an example of a hanger-type sample holding fixture according to the "Whole Article Force Measurement" herein.

The tensile tester is fitted with hanger-type sample holding fixtures (300) as shown in FIG. 7. Each fixture comprises a rigid linear rubber-coated horizontal bar section (302) to prevent sample slippage during testing. The outer bar diameter (including the rubber coating) of the horizontal bar sections is 10.0 mm. The central axes of the horizontal bar sections (302) are configured to remain parallel and in the same vertical plane throughout the test procedure. The gauge circumference is determined by the following equation:

$$\text{Gauge Circumference} = 2 \times (H + D + \pi D/2)$$

where H is the vertical gap between the horizontal bar sections (302), and D is the outer diameter of the bar.

The instrument is set up to go through the following steps:

| | |
|---|---|
| Crosshead Speed | 254.0 mm/min |
| Final Load Point | 19.61 N |
| Hold Time | 0 |
| Number of Cycles | 1 |
| Data Acquisition Rate | 50 Hz |

An article (20) sample is inserted onto the upper horizontal bar section (302) so that the bar passes through the waist opening and one leg opening of the article. The crosshead is raised until the specimen hangs above the lower bar and does not touch lower bar (302). The load cell is tared and the crosshead is lowered to enable the lower bar (302) to be inserted through the waist opening and other leg opening without stretching the article. The article is adjusted so that the longitudinal centerline L1 of the article is in a horizontal plane halfway between the upper and lower bars (302). The center of the side portion in contact with the bar (302) is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the Initial Gauge Circumference at the same speed. The maximum circumference at 19.6N and the force at 70% of the maximum circumference during the loading segment and unloading segment of the test are recorded.

The maximum circumference at 19.6N is defined as the Full Stretch Circumference (mm). The Full Stretch Circumference (mm)×0.7 is defined as the 70% Stretch Circumference. The Waist Circumference Force is defined as the force at 70% stretch circumference during the load (extension) segment of the test. Five samples are analyzed and their average are calculated and reported to the nearest 0.01N, respectively.

Belt Zone Tensile Stress Measurement

The tensile stress (N/m) is calculated by tensile force (N) divided by the specimen width (m). Force may be measured using an Electronic Tensile Tester with a computer interface such as the MTS Criterion C42 running TestWorks 4 Software (available from MTS SYSTEMS (CHINA) CO., LTD) or equivalent instrument. A load cell is chosen so that force results for the samples tested will be between 10% and 90% of capacity of the load cell. The instrument is calibrated according to the manufacturer's instructions. All testing is performed in a room maintained at 23±2° C. and 50±5% relative humidity. The instrument is equipped with single line contact grips at least as wide as the test specimen.

To obtain test specimens, the sample article is cut open along the side seams (32), and the front and belt elastic belt sections (40) are removed from the absorbent main body (38) by separating the bonding between them, and further the waist guard WG is separated from the belt to which it is attached. Cold Spray may be used, paying attention not to make wrinkles in the belt sections. Care is taken not to spray on any belt elastic member (96F, 96S). The obtained elastic belt samples are severed into zones (102, 103, 1031-WGEP, 1031-CP, 104, 105, 106, 108) according to the present invention with care not to cut any elastic member (96F, 96S). Samples are pre-conditioned at 23° C.±2 C.° and 50%±5% relative humidity for two hours prior to testing.

The instrument is set up to go through the following steps. Initial Gauge Length is calculated from the Initial Gauge Circumference which is determined during the Whole Article Force Test using separate identical articles, as described above. Initial Gauge Length=0.5× Initial Gauge Circumference. The final gauge length is calculated from the Full Stretch Circumference which is determined during the Whole Article Force Test, as described above.

| | |
|---|---|
| Crosshead Speed | 254.0 mm/min |
| Data Acquisition Rate | 50 Hz |
| Final Gauge Length | 0.5 × Full Stretch Circumference |
| Hold Time | 0 |
| Number of Cycles | 1 |

One end of the specimen is clamped into the upper clamp and the load is tared. The other end of the specimen is clamped into the lower clamp. Approximately 5 mm of each end of the specimen is behind the contact line of the grip. The test is started and the specimen is extended to the final gauge length at a crosshead speed of 254 mm/min, then immediately returned to the original gauge length at the same speed. The specimen is extended in the article transverse direction during the test. The unload force at 70% of the Final Gauge Length during the unload segments of the test is recorded.

Three articles are analyzed and the unload forces are recorded for each of the zones. The average tensile force (N) is calculated to the nearest 0.01 N for each. The tensile stress for each zone is calculated by the average tensile force (N) divided by the average specimen width (m) and reported to the nearest 0.1 N/m.

In-Bag Stack Height

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within +0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 gram.

Test Procedure

Absorbent article packages are equilibrated at 23±2° C. and 50±2% relative humidity prior to measurement.

The horizontal sliding plate is raised and an absorbent article package is placed centrally under the horizontal sliding plate in such a way that the absorbent articles within the package are in a horizontal orientation (see FIG. 14). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within +0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within +0.5 mm

EXAMPLES

Three different configurations of waist guard pocket were tested. Moreover, a number of absorbent articles as currently available on the market were investigated as comparative examples for the present invention.

Comparative Examples: Commercially Available Baby Diapers

Comparative Example 1: Moony™, purchased in Japan (Size M)

Comparative Example 2: Pampers Baby Dry Pants™ as commercially available in Germany (Size 5)

Comparative Example 4: DM™ Premium Pants Junior, purchased in Germany (13-20 kg)

Comparative Example 3: Mamia Ultra Dry UK™, purchased in UK (Size 4)

Comparative Example 5: Huggies Russia Pants™, purchased in Russia (8-14 kg)

All tested products were PANTS diapers as commercially available first half of 2021. While both Pampers absorbent articles have an absorbent core that did not comprise any airfelt (i.e. no cellulose fibers, instead all absorbent material are superabsorbent polymer particles), all other commercially available absorbent articles had absorbent material that was a mixture of superabsorbent polymer particles and airfelt.

Description of Example 1

The back elastic belt (combination of inner and outer sheet, with elastic strands in between) of Pampers Baby Dry Pants, Size 5, commercially available in the Germany in the first half of 2020 was removed carefully using ice-spray. The remaining article (combination of front elastic belt and absorbent main body) was carefully kept aside. For each absorbent article, a new back elastic belt with a waist guard was made by attaching series of elastic stands between the inner and outer sheet with hot melt adhesive.

For the back elastic belt, 13 gsm nowoven (spunbond-meltblown-spunbond, i.e. SMS) was used as outer sheet which was cut as rectangle with 405 mm in tranverse direction and 240 mm in longitudinal direction. Hot melt adhesive was applied in form of spirals with a basis weight of 5 g/m² across the entire transverse direction and 40 mm longitudinal direction starting 50 mm inboard from the edge of the sheet on outer belt nonwoven. Four 940 dtex elastic stands (first set of elastic strands) were used with 210% elongation rate and glued on the spiral hot melt adhesive in the entire transverse direction and 40 mm in longitudinal direction These four 940 dtex elastic strands were part of the waist guard elastic portion and had different spacing between the elastics. First two elastics has 3 mm spacing between each other whereas third elastic is 7 mm spaced from second elastic and fourth elastic is 7 mm spaced from third elastic. The outer sheet with 50 mm longitudinal dimension was folded immediately adjacent to the location of the innermost elastic strand (i.e. the elastic strand farthest away from the edge of the sheet) in longitudinal direction to encapsulate the 4 elastic strands completely.

Second series of hot melt adhesive was applied in form of spirals with a basis weight of 5 g/m² across entire transverse direction and 35 mm in longitudinal direction starting 20 mm away from fourth 940 dtex elastic (first set of elastics) addition four 470 dtex elastic strands were used with 190% elongation rate and glued on the spiral hot melt adhesive in entire transverse direction. All four elastic strands were 10 mm spaced apart from each other and located inboard in longitudinal direction vs first set of 940 dtex elastic strands.

Third series of hot melt adhesive was applied in form of spirals with a basis weight of 5 g/m² across entire transverse direction and 70 mm in longitudinal direction starting 15 mm away from fourth 470 dtex elastic (second set of elastics) ten 470 dtex elastic strands were used with 240% elongation rate and glued on the spiral hot melt adhesive along the entire transverse direction. These ten elastic strands were glued in the form of five pairs of two elastic strands. For the first four pairs of elastic strands, each elastic strand was 3 mm spaced apart from the other elastic strand of the pair and the first four pairs of elastic strands had 15 mm spacing between the pairs whereas the fifth pair of elastic strands had 10 mm spacing between elastic strands and 10 mm spacing from the elastic strand pair and located inboard in longitudinal direction vs second series of 470 dtex elastic strands. These 5 pairs of elastic strands were cut in transverse direction to create a 100 mm wide intermittent window where no elastic strands were available (or the elastic strands were deprived of their elastic behaviour) in this intermittent non-elastic window and the window was located at the centre location (in transverse direction) of outer sheet. Hot melt adhesive was applied in form of spirals with a basis weight of 5 g/m² across this intermittent non-elastic window region.

10 gsm nowoven (spunbond-meltblown-spunbond, i.e. SMS) was used for the inner sheet which was cut as rectangle with 405 mm in tranverse direction and 126 mm in longitudinal direction. The inner sheet was attached by hot melt adhesive in form of spirals with a basis weight of 5 g/m² over the second and third series of elastic strands on the outer sheet to completely encapsulated the second and third series of elastic strands between inner and outer sheet. This assembly was then attached to the remaining article (combination of front elastic belt and absorbent main body) with the backsheet (garment-facing surface) of the absorbent main body being glued with a hot melt adhesive applied in form of spirals with a basis weight around 5 g/m² at the center in traverse direction and the end edge (50) of the absorbent main body (the one which was originally attached to the "original" back elastic belt of the article) was aligned with the first elastic strand from the second series of elastic strands. The first series of elastic strands with encapsulated assembly was then folded towards the topsheet of the absorbent main body and attached to the topsheet and barrier leg cuffs with hot melt adhesive applied in form of double sided tape with a basis weight of about 25 g/m² in order to create pocket dimensions of 30 mm in longitudinal and 185 mm in transverse direction. Finally, the original front elastic belt and new back elastic belt were attached to each other with mechanical bonding in form of thermal energy to create left and right seams. The absorbent article samples were compacted in a flexible bag at an In Bag Stack Height, i.e. the total caliper of 10 bi-folded articles, of 78 mm for 1 week. Then the bag was opened and the absorbent articles were taken out of the bag and conditioned at least 24 hours prior to any testing at 23° C.+/-2° C. and 50%+/-10% Relative Humidity (RH).

Description of Example 2

Waist Guard Elastic Portion WGEP with 50% Lower Tensile Stress Vs. Example 1

The back elastic belt (combination of inner and outer sheet, with elastic strands in between) of Pampers Baby Dry Pants, Size 5, commercially available in the Germany in the first half of 2020 was removed carefully using ice-spray. The remaining article (combination of front elastic belt and absorbent main body) was carefully kept aside. For each absorbent article, a new back elastic belt with a waist guard was made by attaching series of elastic stands between the inner and outer sheet with hot melt adhesive.

For the back elastic belt, 13 gsm nowoven (spunbond-meltblown-spunbond, i.e. SMS) was used as outer sheet which was cut as rectangle with 405 mm in tranverse direction and 240 mm in longitudinal direction. Hot melt adhesive was applied in form of spirals with a basis weight of 5 g/m² across the entire transverse direction and 40 mm longitudinal direction starting 50 mm inboard from the edge of the sheet on outer belt nonwoven. Four 470 dtex elastic stands (first set of elastic strands) were used with 190% elongation rate and glued on the spiral hot melt adhesive in the entire transverse direction and 40 mm in longitudinal direction These four 470 dtex elastic strands were part of the waist guard elastic portion and had different spacing between the elastics. First two elastics has 3 mm spacing between each other whereas third elastic is 7 mm spaced from second elastic and fourth elastic is 7 mm spaced from third elastic. The outer sheet with 50 mm longitudinal dimension was folded immediately adjacent to the location of the innermost elastic strand (i.e. the elastic strand farthest away from the edge of the sheet) in longitudinal direction to encapsulate the 4 elastic strands completely.

Second series of hot melt adhesive was applied in form of spirals with a basis weight of 5 g/m$^2$ across entire transverse direction and 35 mm in longitudinal direction starting 20 mm away from fourth 940 dtex elastic (first set of elastics) addition four 470 dtex elastic strands were used with 190% elongation rate and glued on the spiral hot melt adhesive in entire transverse direction. All four elastic strands were 10 mm spaced apart from each other and located inboard in longitudinal direction vs first set of 470 dtex elastic strands.

Third series of hot melt adhesive was applied in form of spirals with a basis weight of 5 g/m$^2$ across entire transverse direction and 70 mm in longitudinal direction starting 15 mm away from fourth 470 dtex elastic (second set of elastics) ten 470 dtex elastic strands were used with 240% elongation rate and glued on the spiral hot melt adhesive along the entire transverse direction. These ten elastic strands were glued in the form of five pairs of two elastic strands. For the first four pairs of elastic strands, each elastic strand was 3 mm spaced apart from the other elastic strand of the pair and the first four pairs of elastic strands had 15 mm spacing between the pairs whereas the fifth pair of elastic strands had 10 mm spacing between elastic strands and 10 mm spacing from the 4th elastic strand pair and located inboard in longitudinal direction vs second series of 470 dtex elastic strands. These 5 pairs of elastic strands were cut in transverse direction to create a 100 mm wide intermittent window where no elastic strands were available (or the elastic strands were deprived of their elastic behaviour) in this intermittent non-elastic window and the window was located at the centre location (in transverse direction) of outer sheet. Hot melt adhesive was applied in form of spirals with a basis weight of 5 g/m$^2$ across this intermittent non-elastic window region.

10 gsm nowoven (spunbond-meltblown-spunbond, i.e. SMS) was used for the inner sheet which was cut as rectangle with 405 mm in tranverse direction and 126 mm in longitudinal direction. The inner sheet was attached by hot melt adhesive in form of spirals with a basis weight of 5 g/m$^2$ over the second and third series of elastic strands on the outer sheet to completely encapsulated the second and third series of elastic strands between inner and outer sheet. This assembly was then attached to the remaining article (combination of front elastic belt and absorbent main body) with the backsheet (garment-facing surface) of the absorbent main body being glued with a hot melt adhesive applied in form of spirals with a basis weight around 5 g/m$^2$ at the center in traverse direction and the end edge (50) of the absorbent main body (the one which was originally attached to the "original" back elastic belt of the article) was aligned with the first elastic strand from the second series of elastic strands. The first series of elastic strands with encapsulated assembly was then folded towards the topsheet of the absorbent main body and attached to the topsheet and barrier leg cuffs with hot melt adhesive applied in form of double sided tape with a basis weight of about 25 g/m$^2$ in order to create pocket dimensions of 30 mm in longitudinal and 185 mm in transverse direction. Finally, the original front elastic belt and new back elastic belt were attached to each other with mechanical bonding in form of thermal energy to create left and right seams. The absorbent article samples were compacted in a flexible bag at an In Bag Stack Height, i.e. the total caliper of 10 bi-folded articles, of 78 mm for 1 week. Then the bag was opened and the absorbent articles were taken out of the bag and conditioned at least 24 hours prior to any testing at 23° C.+/−2° C. and 50%+/−10% Relative Humidity (RH).

Description of Example 3

Pocket with 80% Smaller Vs. Example 1

The back elastic belt (combination of inner and outer sheet, with elastic strands in between) of Pampers Baby Dry Pants, Size 5, commercially available in the Germany in the first half of 2020 was removed carefully using ice-spray. The remaining article (combination of front elastic belt and absorbent main body) was carefully kept aside. For each absorbent article, a new back elastic belt with a waist guard was made by attaching series of elastic stands between the inner and outer sheet with hot melt adhesive.

For the back elastic belt, 13 gsm nowoven (spunbond-meltblown-spunbond, i.e. SMS) was used as outer sheet which was cut as rectangle with 405 mm in tranverse direction and 240 mm in longitudinal direction. Hot melt adhesive was applied in form of spirals with a basis weight of 5 g/m$^2$ across the entire transverse direction and 40 mm longitudinal direction starting 50 mm inboard from the edge of the sheet on outer belt nonwoven. Four 940 dtex elastic stands (first set of elastic strands) were used with 210% elongation rate and glued on the spiral hot melt adhesive in the entire transverse direction and 40 mm in longitudinal direction These four 940 dtex elastic strands were part of the waist guard elastic portion and had different spacing between the elastics. First two elastics has 3 mm spacing between each other whereas third elastic is 7 mm spaced from second elastic and fourth elastic is 7 mm spaced from third elastic. The outer sheet with 50 mm longitudinal dimension was folded immediately adjacent to the location of the innermost elastic strand (i.e. the elastic strand farthest away from the edge of the sheet) in longitudinal direction to encapsulate the 4 elastic strands completely.

Second series of hot melt adhesive was applied in form of spirals with a basis weight of 5 g/m$^2$ across entire transverse direction and 35 mm in longitudinal direction starting 20 mm away from fourth 940 dtex elastic (first set of elastics) addition four 470 dtex elastic strands were used with 190% elongation rate and glued on the spiral hot melt adhesive in entire transverse direction. All four elastic strands were 10 mm spaced apart from each other and located inboard in longitudinal direction vs first set of 940 dtex elastic strands.

Third series of hot melt adhesive was applied in form of spirals with a basis weight of 5 g/m$^2$ across entire transverse direction and 70 mm in longitudinal direction starting 15 mm away from fourth 470 dtex elastic (second set of elastics) ten 470 dtex elastic strands were used with 240% elongation rate and glued on the spiral hot melt adhesive along the entire transverse direction. These ten elastic strands were glued in the form of five pairs of two elastic strands. For the first four pairs of elastic strands, each elastic strand was 3 mm spaced apart from the other elastic strand of the pair and the first four pairs of elastic strands had 15 mm spacing between the pairs whereas the fifth pair of elastic strands had 10 mm spacing between elastic strands and 10 mm spacing from the 4th elastic strand pair and located inboard in longitudinal direction vs second series of 470 dtex elastic strands. These 5 pairs of elastic strands were cut in transverse direction to create a 100 mm wide intermittent window where no elastic strands were available (or the elastic strands were deprived of their elastic behaviour) in this intermittent non-elastic window and the window was located at the centre location (in transverse direction) of outer sheet. Hot melt adhesive was applied in form of spirals with a basis weight of 5 g/m² across this intermittent non-elastic window region.

10 gsm nowoven (spunbond-meltblown-spunbond, i.e. SMS) was used for the inner sheet which was cut as rectangle with 405 mm in tranverse direction and 126 mm in longitudinal direction. The inner sheet was attached by hot melt adhesive in form of spirals with a basis weight of 5 g/m² over the second and third series of elastic strands on the outer sheet to completely encapsulated the second and third series of elastic strands between inner and outer sheet. This assembly was then attached to the remaining article (combination of front elastic belt and absorbent main body) with the backsheet (garment-facing surface) of the absorbent main body being glued with a hot melt adhesive applied in form of spirals with a basis weight around 5 g/m² at the center in traverse direction and the end edge (50) of the absorbent main body (the one which was originally attached to the "original" back elastic belt of the article) was aligned with the first elastic strand from the second series of elastic strands. The first series of elastic strands with encapsulated assembly was then folded towards the topsheet of the absorbent main body and attached to the topsheet and barrier leg cuffs with hot melt adhesive applied in form of double sided tape with a basis weight of about 25 g/m² in order to create pocket dimensions of 10 mm in longitudinal and 70 mm in transverse direction. Finally, the original front elastic belt and new back elastic belt were attached to each other with mechanical bonding in form of thermal energy to create left and right seams. The absorbent article samples were compacted in a flexible bag at an In Bag Stack Height, i.e. the total caliper of 10 bi-folded articles, of 78 mm for 1 week. Then the bag was opened and the absorbent articles were taken out of the bag and conditioned at least 24 hours prior to any testing at 23° C.+/−2° C. and 50%+/−10% Relative Humidity (RH).

TABLE 1

| Results of Blowout Test Method and related data for Examples and Comparative Examples | | | | | | | | |
|---|---|---|---|---|---|---|---|---|
| Example/Comparative Example | Example 1 | Example 2 | Example 3 | Comparative Example 1 | Comparative Example 2 | Comparative Example 3 | Comparative Example 4 | Comparative Example 5 |
| Tensile stress of waist guard elastic portion [N/m] | 57 | 29 | 57 | NA | NA | NA | NA | NA |
| Width of Back elastic Belt [mm] | 380 | 410 | 390 | 350 | 370 | 335 | 340 | 335 |
| Length of Absorbent article [mm] | 440 | 450 | 450 | 410 | 450 | 410 | 410 | 440 |
| Diaper weight [grams] | 28.6 | 29.8 | 29.9 | 33 | 28 | 32.3 | 37.7 | 38.4 |
| Blowout Leakage Weight (Avg.) [grams] | 0.67 | 0.17 | 0.90 | 14.02 | 10.84 | 14.00 | 8.93 | 6.20 |
| Blowout Percent Leakage (Avg.) [%] | 0.53 | 0.17 | 0.90 | 9.35 | 10.84 | 9.33 | 5.82 | 4.43 |
| Efficiency Factor = (Blowout Leakage Weight/Diaper Weight) * 100 | 2.33 | 0.56 | 3.01 | 42.49 | 38.73 | 43.34 | 23.70 | 16.15 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal direction and a transverse direction, the absorbent article comprising:
   a front elastic belt, a back elastic belt, and a crotch region, wherein the crotch region extends longitudinally between the front elastic belt and the back elastic belt;
   an absorbent main body connected with the front elastic belt and the back elastic belt extending an entire longitudinal dimension of the crotch region, wherein the absorbent main body comprises: a topsheet, a backsheet, and an absorbent material region sandwiched between;
   a pair of side seams that join the front elastic belt and the back elastic belt to form a waist opening and a pair of leg openings, wherein each side seam comprises a seam length LS;
   wherein the back elastic belt comprises a laminate comprising a plurality of elastic members sandwiched between an outer sheet and an inner sheet, a distal edge, a proximal edge, and zones extending in the transverse direction defined by locations from the distal edge to the proximal edge relative to a percentage of the seam length LS, wherein the distal edge is defined as 0% and the proximal edge is defined as 100%,
   a waist guard extending toward the crotch region from a closed base line toward an open edge, wherein the waist guard is partially bonded to the back elastic belt to define a pocket, wherein the pocket superposes the backsheet and an entirety of the pocket is provided within a location of from 5% to 60% of LS;
   wherein the outer sheet of the back elastic belt is folded at a first fold line and a second fold line to define the waist guard, wherein the first fold line defines the distal edge of the back elastic belt and the second fold line defines the open edge of the waist guard, wherein a first portion of the outer sheet extends longitudinally inwardly toward the crotch region from the first fold line to the second fold line, and wherein a second portion of the outer sheet extends longitudinally away from the crotch region from the second fold line to an edge of the outer sheet, wherein the second portion of the outer sheet is positioned between the first portion of the outer sheet and the inner sheet;
   wherein the waist guard comprises a waist guard elastic portion in an area defining the pocket, wherein an area of the back elastic belt superposing the waist guard elastic portion is defined as a correlated portion, wherein the tensile stress of the waist guard elastic portion is different than that of the correlated portion; and
   wherein the absorbent article comprises a Blowout Percent Leakage of less than 4% when subjected to the Blowout Method herein; and
   wherein the absorbent article comprises a Waist Circumference Force of more than 5.6 N as measured in accordance with the Waist Circumference Force test methods set out herein.

2. The absorbent article of claim 1, wherein the absorbent article has an Efficiency Factor of less than 15% when subjected to the Blowout Method herein.

3. The absorbent article of claim 1, wherein the waist guard elastic portion has a tensile stress of 20-70 N/m as measured in accordance with the Belt Zone Tensile Stress Measurement set out herein.

4. The absorbent article of claim 1, wherein the waist guard elastic portion is elasticized by a plurality elastic strands extending parallel to the transverse direction of the absorbent article.

5. The absorbent article of claim 4 wherein the plurality of elastic strands of the waist guard elastic portion are spaced from the open edge at a distance of not more than 12 mm.

6. The absorbent article of claim 4, wherein a distance between two elastic strands which are closest to the open edge of the waist guard is smaller than a distance between other neighboring elastic strands in the waist guard elastic portion.

7. The absorbent article of claim 4, wherein a number of elastic strands adjacent the open edge is higher than a number of elastic strands away from the open edge.

8. The absorbent article of claim 7, wherein a complete area of the waist guard defining the pocket is the waist guard elastic portion.

9. The absorbent article of claim 1, wherein a longitudinal dimension of the pocket defined as a longest distance between the closed base line to the open edge is from 10 mm to 50 mm.

10. The absorbent article of claim 1, wherein a transverse dimension of the pocket is from 40 mm to 120 mm.

11. The absorbent article of claim 1, wherein the pocket comprises a transverse dimension defined as a longest distance of the pocket extending parallel to a transverse centerline of the absorbent article from a left side edge of the pocket to a right side edge of the pocket, and wherein the transverse dimension of the pocket is from 40% to 96% of a transverse dimension of a transversely extending edge of the backsheet provided in the back waist region.

12. The absorbent article of claim 1, wherein the absorbent main body comprises a pair of leg cuffs disposed along opposing transverse edges extending in the longitudinal direction, wherein the leg cuffs are in active elasticity at the open edge.

13. The absorbent article of claim 1, wherein the Waist Circumference Force according to the Whole Article Force Measurement herein is no more than 9N.

14. The absorbent article of claim 1, wherein the waist guard is partially bonded to the back elastic belt to define the pocket such that a bonded portion of the waist guard superposes the backsheet by at least 5 mm along each of left and right side edges of the pocket, thereby defining the left and right side edges of the pocket; and the bonded portion of the waist guard superposes the backsheet by at least 5 mm along the closed base line of the pocket, thereby defining the closed base line of the pocket.

15. The absorbent article of claim 1, wherein the front elastic belt region is divided into 4 zones spanning in the transverse direction and defined by location from a distal edge to a proximal edge relative to the percentage of the seam length LS, wherein the distal edge of the front elastic belt is considered 0% and the proximal edge of the front elastic belt is considered 100% wherein; 0-25% is a front waist zone, 25-50% is a distal tummy zone, 50-85% is a proximal tummy zone, and 85-100% is a leg zone, wherein the proximal tummy zone comprises a higher tensile stress than other zones in the front elastic belt.

16. The absorbent article of claim 1, wherein the absorbent article has a dry weight of less than 50 g.

* * * * *